US012708390B2

(12) United States Patent
Berg et al.

(10) Patent No.: US 12,708,390 B2
(45) Date of Patent: Aug. 18, 2026

(54) THROMBECTOMY MANIPULATION CONTROLLER AND METHODS FOR SAME

(71) Applicant: Endologix LLC, Santa Rosa, CA (US)

(72) Inventors: Jordan Berg, Eden Prairie, MN (US); Peter Bo, Eden Prairie, MN (US); Dan Johnson, Eden Prairie, MN (US)

(73) Assignee: Endologix LLC, Santa Rosa, CA (US)

(*) Notice: Subject to any disclaimer, the term of this patent is extended or adjusted under 35 U.S.C. 154(b) by 663 days.

(21) Appl. No.: 18/116,979

(22) Filed: Mar. 3, 2023

(65) Prior Publication Data

US 2023/0285041 A1 Sep. 14, 2023

Related U.S. Application Data

(60) Provisional application No. 63/316,796, filed on Mar. 4, 2022.

(51) Int. Cl.

*A61B 17/221* (2006.01)
*A61M 25/06* (2006.01)
*A61M 39/10* (2006.01)

(52) U.S. Cl.

CPC ....... *A61B 17/221* (2013.01); *A61M 25/0662* (2013.01); *A61M 39/1011* (2013.01);

(Continued)

(58) Field of Classification Search

CPC .......... A61B 17/12022; A61B 17/1204; A61B 17/12109; A61B 17/12131;

(Continued)

(56) References Cited

U.S. PATENT DOCUMENTS 6,214,026 B1 * 4/2001 Lepak .................... A61F 2/013 604/104
9,283,066 B2 3/2016 Hopkins et al.

(Continued)

FOREIGN PATENT DOCUMENTS

EP 4079239 10/2022
WO 2023168028 9/2023
WO 2024184276 9/2024

OTHER PUBLICATIONS

"International Application Serial No. PCT US2023 014423, Invitation to Pay Additional Fees mailed Apr. 28, 2023", 2 pgs.

(Continued)

*Primary Examiner* — Kankindi Rwego
(74) *Attorney, Agent, or Firm* — Foley & Lardner LLP

(57) ABSTRACT

A thrombectomy assembly includes a sheath catheter having a sheath lumen and a trumpet catheter including a trumpet lumen. The trumpet catheter is received in the sheath lumen. A manipulation controller is coupled with the trumpet catheter and the sheath catheter. The manipulation controller includes a sheath actuator coupled with the sheath catheter and a catheter lock. The catheter lock includes a deformable collet having a collet passage configured to receive a capture catheter therein. The sheath actuator is configured to move the sheath catheter between a deployed configuration with the sheath actuator retracted from a deployable trumpet of the trumpet catheter and a stored configuration with the sheath actuator covering the deployable trumpet. The deformable collet is configured to transition between a locked configuration with the deformable collet compressed around the capture catheter and an unlocked configuration with the deformable collet expanded around the capture catheter.

32 Claims, 15 Drawing Sheets

(52) U.S. Cl.
CPC ................ *A61B 2017/2215* (2013.01); *A61M 2025/0681* (2013.01)

(58) Field of Classification Search
CPC ........ A61B 17/12172; A61B 17/12136; A61B 17/22031; A61B 17/22032; A61B 17/221; A61B 17/2841; A61B 17/2902; A61B 2017/00336; A61B 2017/00367; A61B 2017/00371; A61B 2017/00376; A61B 2017/0038; A61B 2017/00384; A61B 2017/00389; A61B 2017/00393; A61B 2017/0057; A61B 2017/22034; A61B 2017/22035; A61B 2017/22051; A61B 2017/22079; A61B 2017/22094; A61B 2017/2212; A61B 2017/2215; A61B 2017/291; A61B 2017/2916; A61B 2017/2924; A61B 1/00064; A61M 25/0067; A61M 25/0074; A61M 2025/0079; A61M 2025/0681; A61M 2205/0272; A61M 29/00; A61M 29/02; A61M 2029/025; A61M 39/1011; A61F 2/9517
USPC ......................................... 606/128, 159, 200
See application file for complete search history.

(56) References Cited

U.S. PATENT DOCUMENTS

| | | | |
|---|---|---|---|
| 2006/0047286 A1 | 3/2006 | West | |
| 2012/0165858 A1 | 6/2012 | Eckhouse et al. | |
| 2012/0239077 A1 | 9/2012 | Zaver et al. | |
| 2016/0199617 A1 | 7/2016 | Pigott | |
| 2016/0256180 A1 | 9/2016 | Vale et al. | |
| 2017/0325830 A1 | 11/2017 | Martin et al. | |
| 2018/0296315 A1 | 10/2018 | Nguyen et al. | |
| 2019/0133616 A1 | 5/2019 | Sachar et al. | |
| 2020/0029984 A1 | 1/2020 | Wang et al. | |
| 2020/0178991 A1 | 6/2020 | Greenhalgh et al. | |
| 2021/0068620 A1 | 3/2021 | Walen et al. | |
| 2021/0128893 A1 | 5/2021 | Twomey et al. | |
| 2021/0186543 A1 | 6/2021 | Wallace et al. | |
| 2021/0378694 A1* | 12/2021 | Thress | A61B 17/221 |

OTHER PUBLICATIONS

"International Application Serial No. PCT US2023 014423, International Search Report mailed Jul. 28, 2023", 4 pgs.
"International Application Serial No. PCT US2023 014423, Written Opinion mailed Jul. 28, 2023", 10 pgs.
"International Application Serial No. PCT EP2024 055504, International Search Report mailed Jul. 2, 2024", 6 pgs.
"International Application Serial No. PCT EP2024 055504, Written Opinion mailed Jul. 2, 2024", 9 pgs.
"International Application Serial No. PCT US2023 014423, International Preliminary Report on Patentability mailed Sep. 19, 2024", 12 pgs.
"European Application Serial No. 23763949.7, Extended European Search Report mailed May 8, 2025", 7 pgs.

* cited by examiner

THROMBECTOMY MANIPULATION CONTROLLER AND METHODS FOR SAME

PRIORITY APPLICATION

This application claims the benefit of priority to U.S. Provisional Patent Application Ser. No. 63/316,796, filed Mar. 4, 2022, the content of which is incorporated herein by reference in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright Surmodics MD, LLC of Eden Prairie, Minnesota, USA. All Rights Reserved.

TECHNICAL FIELD

This document pertains generally, but not by way of limitation, to catheters and thrombectomy procedures.

BACKGROUND

Thrombectomy procedures treat thrombus within the vasculature with a thrombectomy assembly. In some examples, a thrombectomy assembly delivers one or more capture features, such as a cage, filter or the like to a treatment site. The capture features separate thrombus from vessel walls, collect thrombus from within the vessel, and capture the thrombus for extraction with the remainder of the thrombus assembly. The capture features are coupled with an associated catheter (e.g., guidewire, tube or the like), for instance at the catheter distal end, forming a capture catheter.

In some examples, the capture catheter is received within a trumpet catheter. The trumpet catheter includes a deployable trumpet coupled along another catheter to form the trumpet catheter. The trumpet catheter is in turn received within a sheath catheter, and the sheath catheter surrounds the trumpet and capture features (of the capture catheter).

In operation, the capture catheter having the capture features and a sleeve extending over the capture features is moved distally relative to the trumpet catheter and the thrombus. The sleeve is withdrawn to reveal the capture features and permit their deployment distal to the thrombus. The trumpet catheter and sheath catheter are positioned, for instance, proximal to the thrombus, and the sheath catheter is withdrawn to reveal the trumpet while the capture catheter and trumpet catheter are held static.

Movement of the sheath catheter relative to the trumpet controls deployment of the trumpet. Movement of one or both of the trumpet catheter or capture catheter, in another example, controls retrieval of the trumpet or capture features with the sheath catheter. Accordingly, selective control (e.g., movement, holding static, moving some components together and maintaining others static or the like) of each of the three components; capture catheter, trumpet catheter and sheath catheter; relative to each other coordinates the operation of the components to capture thrombus, collect the captured thrombus (and the capture features and trumpet), and extract the thrombus assembly and thrombus from the vasculature.

SUMMARY

The present inventors have recognized, among other things, that a problem to be solved can include coordinating control of multiple components of a thrombectomy assembly with a limited number of personnel, for instance a single technician or caregiver. A thrombectomy assembly includes multiple components that are operated in selective permutations of coordinating movement (movement together), relative movement, and combinations of both coordinating and relative movement.

For instance, a capture catheter including one or more capture features (e.g., cages, filters or the like) stowed in a deployment sleeve (a separate catheter) is delivered through a procedural sheath to a treatment site and distal to thrombus (including thrombus, emboli, clot or the like). The deployment sleeve is withdrawn to reveal the capture features and permit their expansion to a deployed configuration. A sheath catheter containing the trumpet catheter is delivered through the procedural sheath to the treatment site and proximal to the thrombus. One or more clinicians hold the separate capture catheter static and hold the trumpet catheter static while proximally retracting the sheath catheter to reveal the trumpet and permit its deployment. The thrombus is interposed between the deployed capture features of the capture catheter and the deployed trumpet of the trumpet catheter.

Capture of thrombus with the capture catheter is accomplished with proximal movement of the capture catheter and the capture features through thrombus while the trumpet catheter and sheath catheter are held relatively static. Collection of the capture features and captured thrombus is conducted with continued proximal movement of the capture catheter to draw the capture features into the trumpet along with the captured thrombus.

Retrieval of the trumpet catheter, capture catheter and the captured thrombus includes holding each of the trumpet catheter, capture catheter (nested in the trumpet) and the sheath catheter static relative to each other while also moving each of these trumpet catheter, the capture and the sheath catheter proximally relative to (and into) the procedural sheath where each of the trumpet, capture features and captured thrombus are compressed and withdrawn through the vasculature. Holding the trumpet catheter, capture catheter and the sheath catheter static relative to each other minimizes shearing therebetween that may free particulate thrombus from the catheters and permit its re-entry to the vessel.

The movement of each of the thrombectomy assembly components can be difficult and is aggravated by coordination of components relative to each other to conduct the various operations. One solution is to use multiple clinicians or caregivers (operators) to operate the thrombectomy assembly in concert. Each of the operators manipulates one, or potentially two, of the thrombectomy assembly components and coordinates the operation with the remaining thrombectomy assembly components operated by other operators. Operating in concert involves one or more of training, experience and precise coordination of movement between each of the operators to ensure specified deployment of features of the assembly, capture of thrombus, retrieval of the features, and retraction and withdrawal of the thrombectomy assembly (e.g., into a procedural sheath and out of the vasculature). Operators in some examples crowd the thrombectomy assembly, vascular access site, and the presiding physician to access and operate the thrombectomy assembly. Accordingly, a thrombectomy procedure with this type of coordination is laborious and complex.

The present subject matter can help provide a solution to this problem, for instance with a thrombectomy assembly that consolidates control of the assembly into a manipulation controller that is readily operated by a clinician with minimal assistance (e.g., little or none) from other clinicians or operators. The manipulation controller includes control interfaces that permit the movement of the thrombectomy assembly components relative to each other and also permits coordinated operation of components (e.g., movement and manipulation together), and various permutations of coordination and relative movement as specified by the clinician.

In one example, the manipulation controller consolidates operation to control interfaces on a handle, hub or fixture coupled with each of the capture catheter, trumpet catheter and sheath catheter. The manipulation controller merges functionality provided with separate components. For instance, translation, rotation, static coupling between catheters, sliding coupling between catheters, controlled variation of the same, as examples of coordinated and relative movements, are provided with the manipulation controller. The clinician is thereby able to operate the thrombectomy assembly alone or with minimal assistance (e.g., including no assistance or decreased assistance) while providing full functionality for the thrombectomy assembly previously achieved with coordinated operation by multiple personnel.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
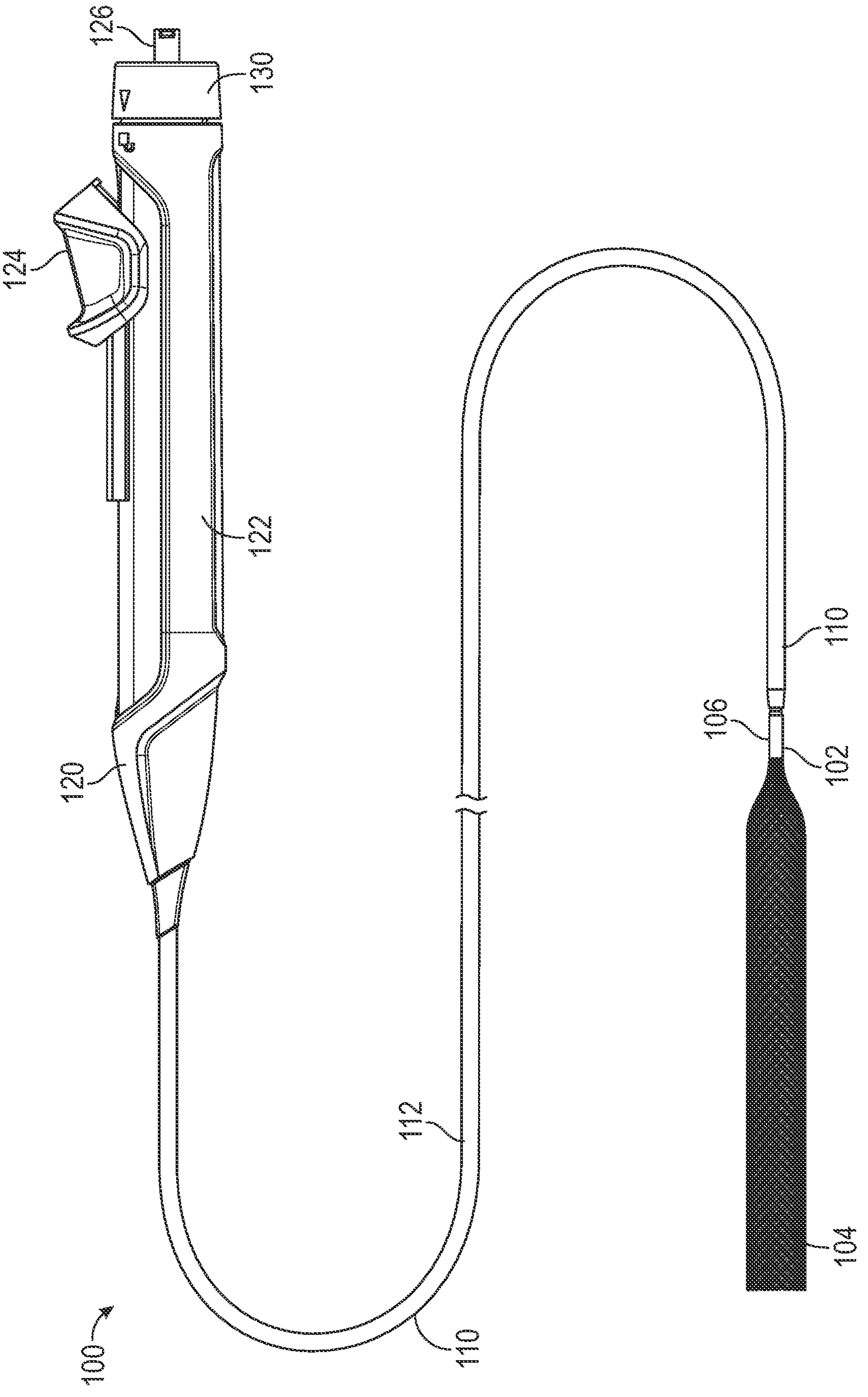
FIG. 1 is a side view of one example of a thrombectomy assembly having an example manipulation controller.

FIG. 1 is a side view of one example of a thrombectomy assembly 100 including a manipulation controller 120 coupled with one or more catheters including a sheath catheter 110 and a trumpet catheter 102. As described herein, the manipulation controller 120 of the thrombectomy assembly 100 controls various aspects of each of the trumpet catheter 102 and the sheath actuator 110.

As shown in FIG. 1, each of the sheath catheter 110 and the trumpet catheter 102 are coupled with the manipulation controller 120. The manipulation controller includes a controller housing 122 that receives and couples with the catheters 102, 110. The manipulation controller 120 includes a sheath actuator 124 configured to move one or more components of the thrombectomy assembly 100 relative to each other. In one example, the sheath actuator 124 is coupled with the sheath shaft 112 of the sheath catheter 110. Accordingly, movement of the sheath actuator 124 moves the sheath catheter 110 (and the sheath shaft 112) relative to the trumpet catheter 102.

As further shown in FIG. 1, the manipulation controller 120 is, in another example, coupled with the trumpet catheter 102. As shown, the trumpet catheter 102 includes a deployable trumpet 104, for instance, having the cylindrical and conical portions shown in FIG. 1. The trumpet 104, in one example, is constructed with a mesh or braided material such as wires, filars, elongate filaments or the like to provide a collection feature configured to extend into the vasculature, deploy along the vasculature, and receive one or more thrombus, clot or the like as well as capture features (e.g., of a capture catheter). The trumpet 104, shown in FIG. 1, is coupled with the trumpet shaft 106 and the trumpet shaft 106 in turn extends through the sheath catheter 110 to the manipulation controller 120.

As further shown in FIG. 1, the manipulation controller 120 includes the sheath actuator 124. As previously described, the sheath actuator 124 is, in one example, coupled with the sheath catheter 110 and movement of the sheath actuator 124 moves the sheath actuator 110, for instance, between retracted and extended positions. In the retracted position the sheath catheter 110 is withdrawn relative to the trumpet 104, and in the extended position the sheath catheter 110 is deployed over the trumpet 104. As described herein, while the sheath catheter is deployed over the trumpet 104 the trumpet 104 is maintained in a slender profile, for instance, to permit navigation through the vasculature to a location of interest.

As further shown in FIG. 1, the manipulation controller 120, in another example, includes an introduction port 126.

The introduction port 126 extends toward and is in communication with one or more lumens of the sheath catheter 110, the trumpet catheter 102 or the like. For instance, in one example, one or more instruments are provided through the introduction port 126. In another example, the trumpet catheter 102 and sheath catheter 110 are fed over instruments positioned in the vasculature and the thrombectomy assembly 100 (including the catheters 102, 110) is fed over those instruments and a trailing end of those instruments extends from the introduction port 126.

As further shown in FIG. 1, the manipulation controller 120, in another example, includes a catheter lock 130. As described herein, the catheter lock 130 facilitates the coupling and decoupling of the thrombectomy assembly 100 to one or more instruments of the remainder of the thrombectomy assembly 100, for instance, extending through one or more of the introduction port 126, the catheters including, but not limited to, the trumpet catheter 102, the sheath catheter 110 or the like. As described herein, with the catheter lock 130 in a locked configuration instruments extending through the manipulation controller 120 are held static. The catheter lock 130 in the locked configuration permits consolidated movement of the components of the thrombectomy assembly 100 together, for instance, as a unitary system. That is to say, in one example, with the catheter lock 130 activated and in a locked configuration, movement at the manipulation controller 120, including one or more of rotation or transition of the manipulation controller 120 correspondingly moves the sheath catheter 110, the trumpet catheter 102 as well as one or more instruments extending through the manipulation controller 120.

Figure 2A:
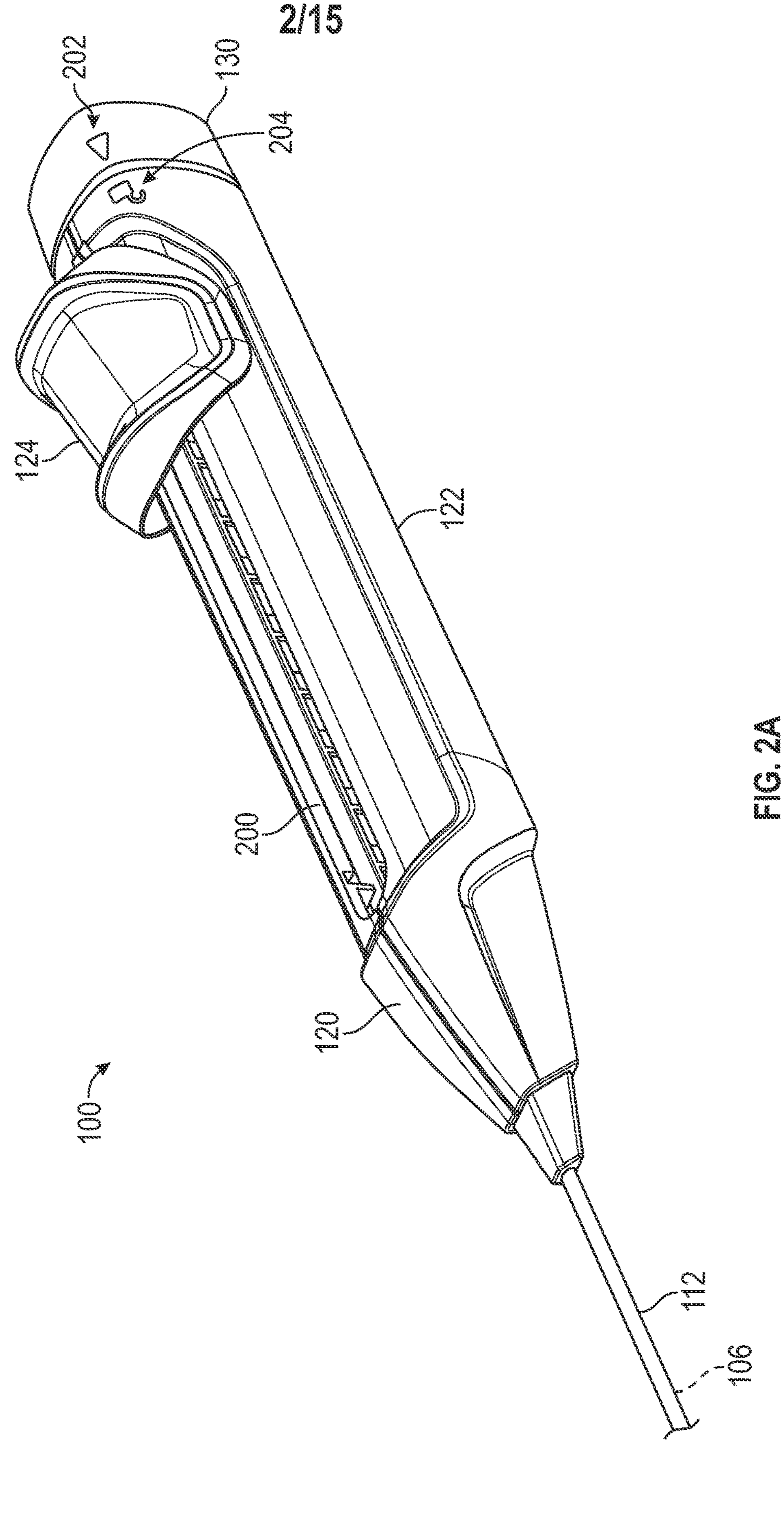
FIG. 2A is a first perspective view of the manipulation controller of FIG. 1.

FIG. 2A shows a portion of the thrombectomy assembly 100 including the manipulation controller 120. In this example, the manipulation controller 120 includes the sheath actuator 124 in a retracted or first position relative to the remainder of the manipulation controller 120 including the controller housing 122. For instance, in FIG. 2A, the sheath actuator 124 is withdrawn or retracted along an actuator track 200. In this configuration, with the sheath actuator 124 withdrawn the sheath shaft 112 of the sheath catheter 110 (previously shown in FIG. 1) is retracted relative to the deployable trumpet 104 and the trumpet 104 is permitted to expand, for instance as shown in FIG. 1. As described herein, the sheath actuator 124 is, in one example, coupled with the sheath shaft 112 and permits movement of the sheath catheter 110 (and the sheath shaft 112) relative to the controller housing 122 and the trumpet catheter 102 having the trumpet shaft 106 coupled with a different component of the controller housing 122, for instance, a portion of the catheter lock 130. Movement of the sheath actuator 124 accordingly moves the sheath shaft 112 relative to the trumpet shaft 106.

Referring again to FIG. 2A, another view of the catheter lock 130 is provided. In the example shown in FIG. 2A, an example of a lock indicator 202 is provided with the catheter lock 130 and an unlocked indicia 204 is provided on the controller housing 122. The catheter lock 130 with the lock indicator 202 aligned with or proximate to the unlocked indicia 204 indicates that the catheter lock 130 is in an unlocked configuration and accordingly instruments coupled with the catheter lock 130 are readily moveable relative to the remainder of the thrombectomy assembly 100 including the manipulation controller 120 as well as the sheath catheter 110 and the trumpet catheter 102. For instance, instruments extending through the catheter lock 130 in the unlocked configuration are readily translated, rotated or the like relative to the manipulation controller 120 and the catheters 102, 110.

Figure 2B:
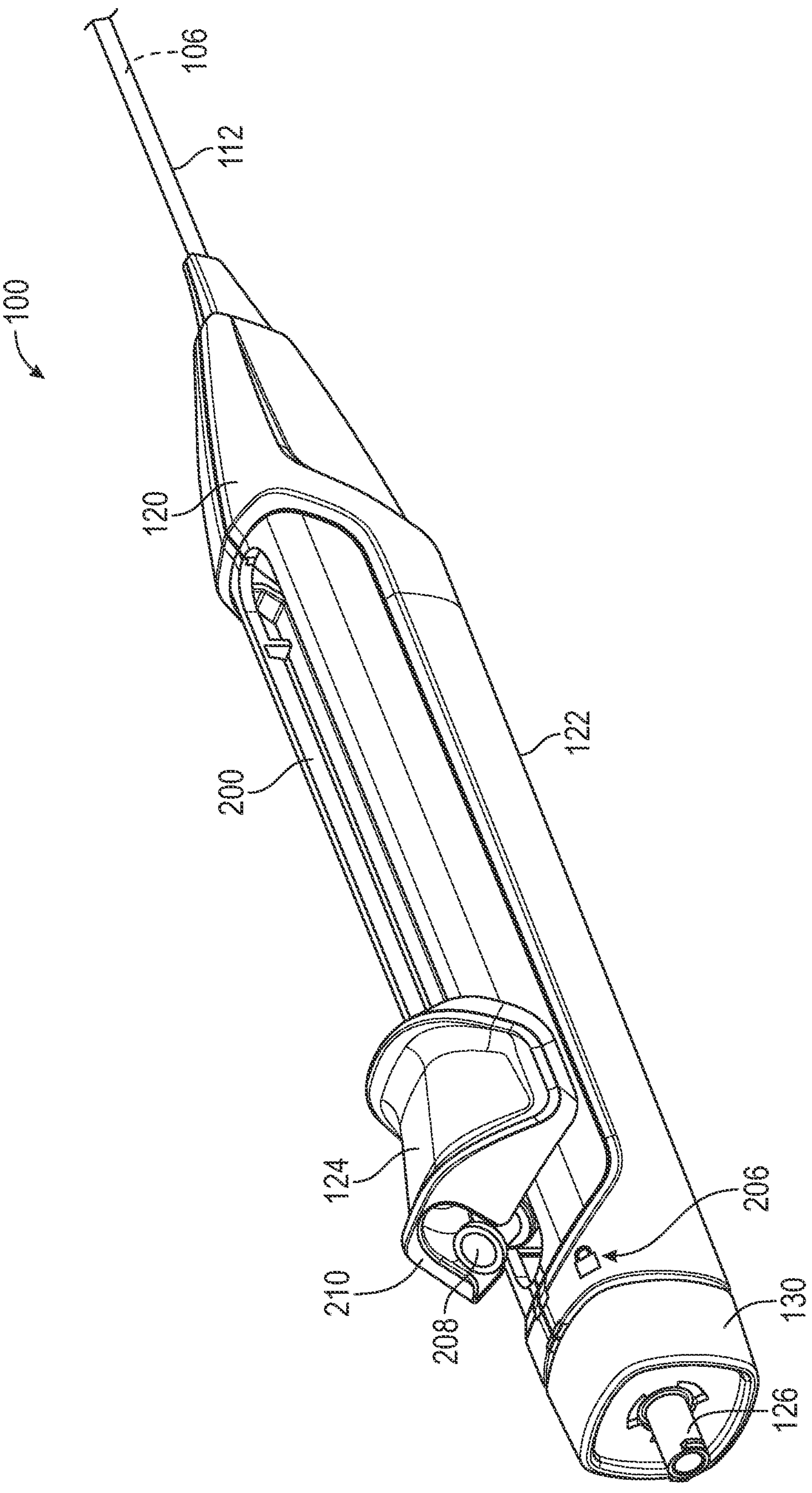
FIG. 2B is a second perspective view of the manipulation controller of FIG. 1.

FIG. 2B is another perspective view of a portion of the thrombectomy assembly 100 again showing the manipulation controller 120. As in the previous example, the sheath actuator 124 is in the retracted position corresponding to withdrawal or retraction of the sheath shaft 112 (coupled with the sheath actuator 124) relative to the trumpet shaft 106 and thereby permitting deployment of the trumpet 104 into the deployed configuration shown in FIG. 1.

In the view shown in FIG. 2B, the sheath actuator 124 is shown with one example of a port cowl 210 proximate to a flushing port 208. As described herein, the flushing port 208 is, in one example, in communication with one or more of the sheath shaft 112, the trumpet shaft 106 as well as intervening gaps or spaces therebetween. The flushing port 208 permits the introduction of flushing fluid, such as saline (optionally thrombolytics, contrast agents or the like) into the gap between the sheath shaft 112 and the trumpet shaft 106. Flushing of the sheath catheter 110 and the trumpet catheter 102 and the spaces therebetween flushes or evacuates air, particulate or the like prior to introduction of the thrombectomy assembly 100 to vasculature.

As further shown in FIG. 2B, the introduction port 126 extends into the controller housing 122. In this example, the introduction port 126 extends through the catheter lock 130 and, as described herein, instruments provided through the introduction port similarly extend through the catheter lock 130. One example of a locked indicia 206 is provided in FIG. 2B. In one example, with the lock indicator 202 shown in FIG. 2A rotated into alignment or proximate to the locked indicia 206, the catheter lock 130 is transitioned to a locked configuration and accordingly one or more instruments provided through the catheter lock 130 and extending through the manipulation controller 120 (as well as the sheath catheter 110 and the trumpet catheter 102) are held statically relative to the other components of the thrombectomy assembly 100. Accordingly, in the locked configuration movement of the manipulation controller 120 including one or more of translation or rotation of the manipulation controller 120, for instance, by manual manipulation by an operator, clinician or the like correspondingly moves the components of the thrombectomy assembly 100 in a unitary or consolidated fashion. That is to say, each of the trumpet catheter 102, sheath catheter 110, the manipulation controller 120 and instruments therein are moved together, for instance, including, but not limited to, consolidated translation, rotation or both.

Figure 3:
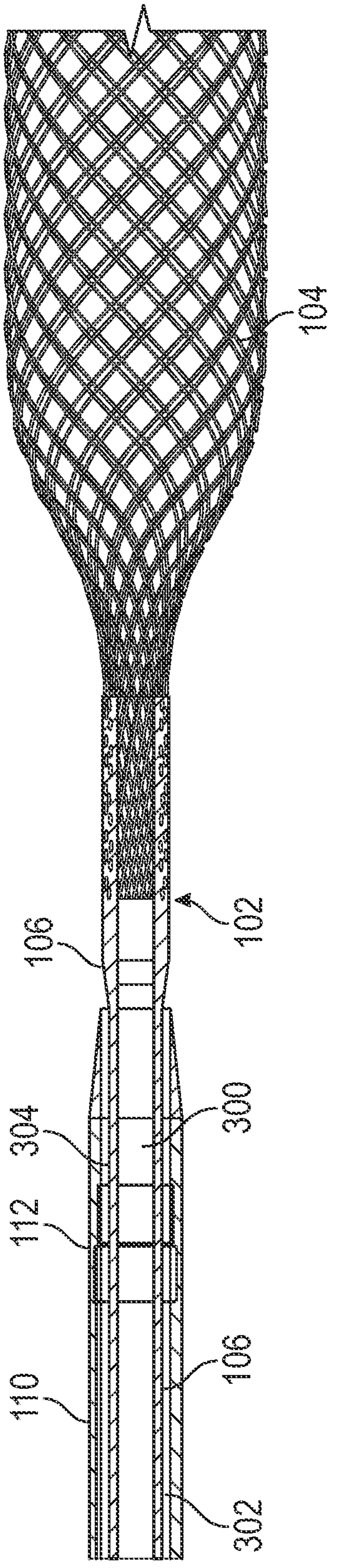
FIG. 3 is a cross sectional view of a distal portion of the thrombectomy assembly of FIG. 1.

FIG. 3 shows a sectional view of a portion of the thrombectomy assembly 100 including portions of the trumpet catheter 102 and the sheath catheter 110. As shown in FIG. 3, a trumpet catheter distal portion 304 is coupled with the trumpet 104. In one example, the trumpet 104 is constructed with, but not limited to, one or more shape memory materials such as Nitinol, piano wire, meshes, filaments, filars or the like that are configured to expand when permitted, for instance, after retraction of the sheath shaft 112 from over top of the trumpet 104. Movement of the trumpet catheter distal portion 304 (or conversely, movement of the sheath catheter 110 relative to the trumpet catheter distal portion 304) reveals the trumpet 104 and permits its deployment into the deployed configuration shown in FIG. 3.

As further shown in FIG. 3, the trumpet catheter 102 is positioned within a sheath lumen 302 of the sheath catheter 110. The sheath shaft 112 extends around the trumpet catheter 102 and when retracted, as shown in FIG. 3, permits the deployment of the trumpet 104. As further shown in FIG. 3, the trumpet shaft 106 of the trumpet catheter 102 includes a trumpet lumen 300 therein. In one example, the trumpet lumen 300 receives or is provided with one or more supplemental instruments of the thrombectomy assembly 100 including, but not limited to, a capture catheter having one or more cages, filters or the like. The capture catheter including, for instance, its cages, filters or the like, after deployment, are retracted through one or more thrombus, clot, particulate or the like (collectively referred to as thrombus) and are drawn into the trumpet 104. As further discussed herein, the system including the trumpet 104 in the deployed configuration as well as the cages, filters or the like of the capture catheter as well as thrombus trapped between the trumpet 104 and the cages is retracted into the remainder of the thrombectomy assembly 100 including, for instance, a procedure sheath or catheter provided in the vasculature. Retraction into one or more of these components (e.g., with retraction provided by the manipulation controller 112) compresses the trumpet 104, the cages therein as well as the captured thrombus to permit withdrawal of the thrombus or clot from the vasculature and out of the patient.

Figure 4A:
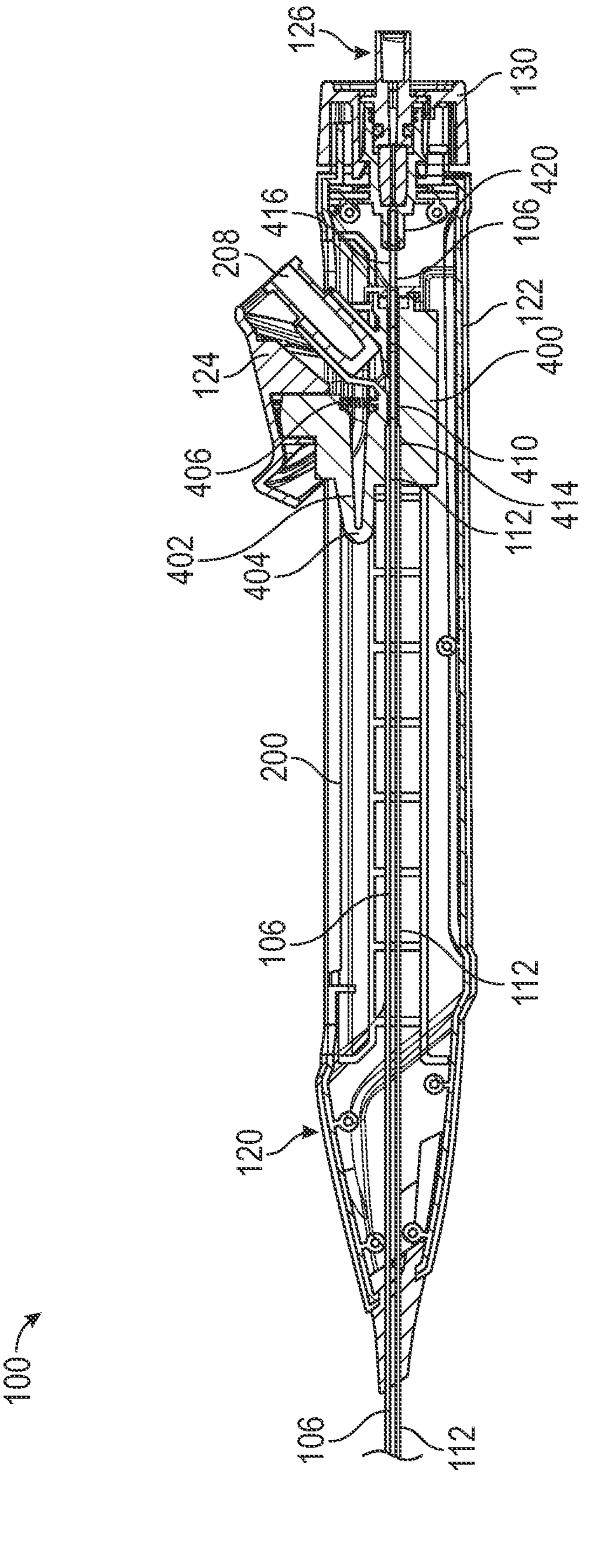
FIG. 4A is a cross sectional view of the manipulation controller of FIG. 1.
Figure 4B:
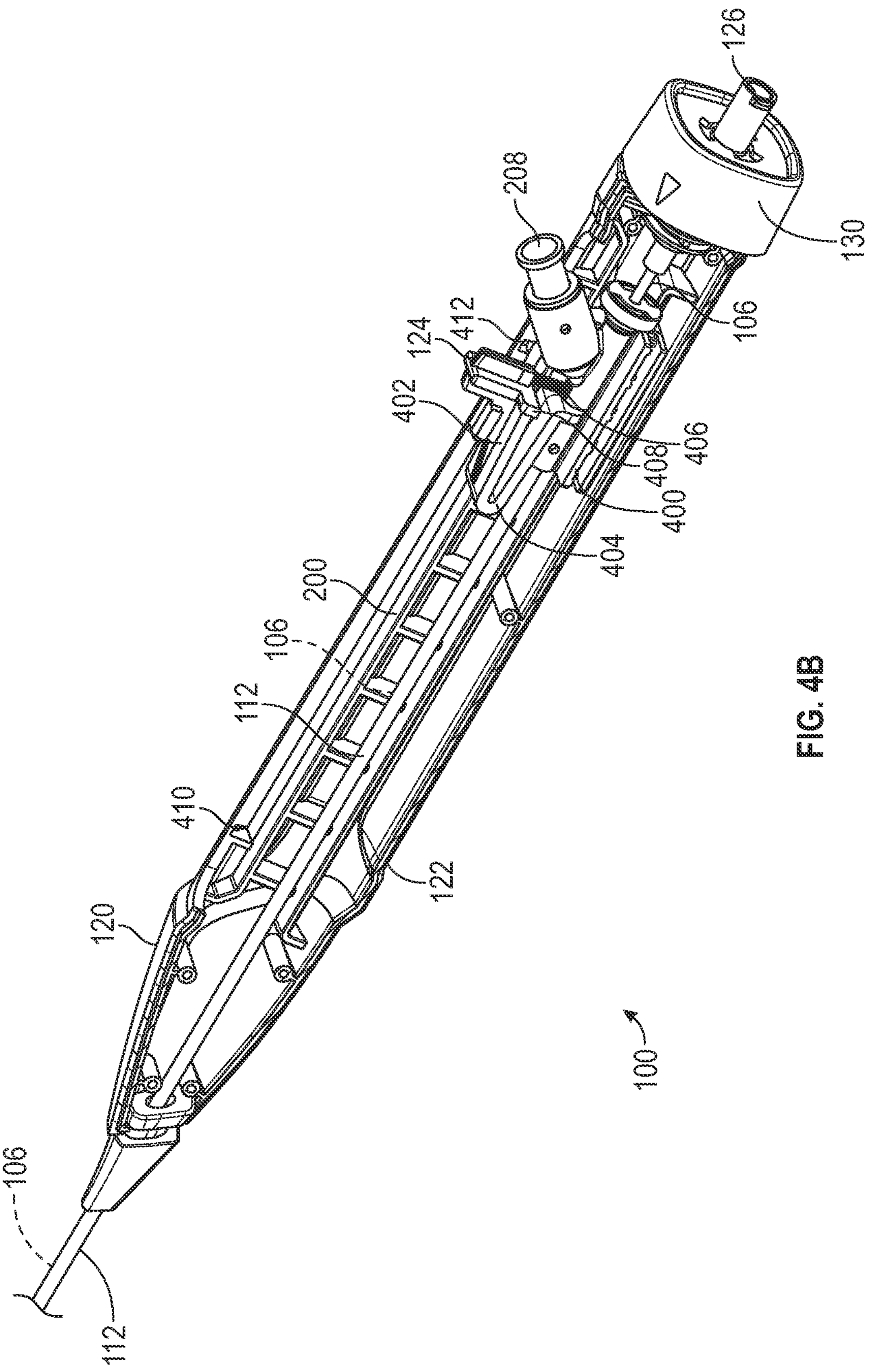
FIG. 4B is a partial sectional view of the manipulation controller of FIG. 1.

FIGS. 4A and 4B are cross sectional and partial sectional views of a portion of the thrombectomy assembly 100 including the manipulation controller 120. As shown in FIG. 4A and FIG. 4B, the manipulation controller 120 receives and is coupled with various catheters of the thrombectomy assembly including, for instance, the sheath shaft 112 of the sheath catheter 110 and the trumpet shaft 106 of the trumpet catheter 102. In one example, the sheath shaft 112 is the exterior or outer shaft shown in FIGS. 4A and 4B and is coupled with the sheath actuator 124. For instance, the sheath actuator 124 includes an actuator shuttle 400 having a sheath seat 414 that receives and couples with the sheath shaft 112, such as a proximal portion of the sheath shaft therein. Conversely, the trumpet shaft 106 of the trumpet catheter 102 is slidably received or nested within the sheath shaft 112 and extends through the sheath actuator 124. The trumpet shaft 106 is coupled with another portion of the controller housing 122 of the manipulation controller 120 including, for instance, a trumpet seat 420. As previously described, with the sheath shaft 112 coupled with the sheath actuator 124, movement of the sheath actuator 124 correspondingly moves the sheath catheter 110 relative to the trumpet catheter 102 including the trumpet 104. The relative movement controlled from the manipulation controller 120 permits covering and uncovering of the trumpet 104, by movement of the sheath shaft 112 of the sheath catheter 110.

As previously discussed and shown in FIGS. 4A and 4B, the trumpet shaft 106, in an example, extends through the sheath actuator 124 and is seated with a portion of the controller housing 122 at the trumpet seat 420. In an example, the trumpet seat 420 is a component or included with a portion of the catheter lock 130. The trumpet seat 420 holds the trumpet shaft 106 static relative to the remainder of the controller housing 122 and the sheath catheter 110 is slidably movable along the trumpet shaft 106 with the sheath actuator 124. As shown in FIG. 4A, the trumpet shaft 106 of the trumpet catheter 102 extends through the sheath actuator 124 (e.g., through a trumpet catheter passage 506 shown in FIG. 5) and the sheath actuator 124 and sheath shaft 112 are slidable over and along trumpet shaft 106.

The sheath actuator 124 example shown in FIGS. 4A, B includes an actuator shuttle 400 moveable within the controller housing 122, for instance, along the actuator track 200. The actuator shuttle 400, in one example, has a planar or plate-type shape to facilitate movement of the sheath actuator 124 therein. The controller housing 122 includes recesses, fittings or the like that provide a passage for the actuator shuttle 400 to retain the sheath actuator 124 coupled with the housing 122 while permitting its movement.

As further shown, the sheath actuator 124, including the actuator shuttle 400, extends around the sheath shaft 112 and provides, in one example, the sheath seat 414 shown in FIG. 4A. The sheath shaft 112 is received within the actuator shuttle 400 and fixed to the actuator shuttle 400 to ensure movement of the sheath actuator 124 is translated into movement of the sheath catheter 110 including the sheath shaft 112.

As further shown in FIGS. 4A and 4B, the sheath actuator 124, in another example, includes a shuttle toggle 402 that is movable in elevation and depression relative to the remainder of the sheath actuator 124 and the manipulation controller 120. As described herein, in one example, the shuttle toggle 402 of the sheath actuator 124 includes one or more anchors 408 (see FIG. 4B) that selectively seat within corresponding anchor sockets, such as the anchor sockets 410, 412. As described herein, seating of the one or more anchors 408 and the corresponding anchor sockets 410, 412 cooperatively hold the sheath actuator 124 (and the associated sheath catheter 110) static, for instance one or more of translationally or rotationally relative to the manipulation controller 120. Movement of the manipulation controller 120 in one or more of translation or rotation is thereby readily transmitted to the sheath catheter 110.

In one example, one or more biasing elements, such as the anchor biasing elements 404, 406 shown in FIGS. 4A, B are provided with the sheath actuator 124 to bias the shuttle toggle 402 from a depressed position to an elevated position with the anchors 408 received within the respective anchor sockets 410, 412 (e.g., with the sheath actuator 124 longitudinally proximate to the sockets). Accordingly, in one example, a default or biased configuration of the sheath actuator 124 in the proximal or distal locations along the actuator track 200 is a locked or static configuration with the one or more anchors 408 received within the corresponding anchor sockets 410 or anchor sockets 412 according to the position of sheath actuator 124 (e.g., proximal or distal). In one example, the anchor biasing element 404 includes a living hinge, for instance, including the material of the sheath actuator 124, such as a deformable plastic, metal, composite or the like. In another example, the sheath actuator 124 includes the biasing element 406 such as, but not limited to, a coil spring, leaf spring, torsion spring, elastically deformable feature or the like. Optionally, the manipulation controller 120 includes one or more of the anchor biasing elements 404, 406 and the one or more elements are used individually or alternatively together to bias a component of the sheath actuator 124, such as the shuttle toggle 402.

As further shown in FIGS. 4A and 4B, the manipulation controller 120 includes one example of the catheter lock 130. In this example, the catheter lock 130 includes the trumpet seat 420 coupled with the trumpet shaft 106. As described herein, the trumpet shaft 106 received at the trumpet seat 420 is, in one example, in communication with or aligned with one or more ports or passages extending through the catheter lock 130, for instance, into the introduction port 126. Instruments received through the introduction port 126 pass through the catheter lock 130 and the trumpet seat 420 and are received in the trumpet shaft 106. While the catheter lock 130 is in an unlocked configuration instruments coupled with the lock are permitted to move relative to the manipulation controller 120 as well as one or more of the other components of the thrombectomy assembly 100 including, but not limited to, the trumpet catheter 102 and the sheath catheter 110. Conversely, with the catheter lock 130 in a locked configuration, the catheter lock 130 holds instruments coupled with the lock statically and movement of the thrombectomy assembly 100 is consolidated. For instance, motion or movement provided to the manipulation controller 120, such as rotation, translation or the like initiated by the clinician or physician at the controller 120, is transmitted from the controller 120 to each of the sheath catheter 110, trumpet catheter 102 as well as instruments coupled with the catheter lock 130 in the locked configuration. Accordingly, the clinician, physician readily moves, manipulates, or orients the thrombectomy assembly 100 with consolidated movement provided through the manipulation controller 120 having the catheter lock 130.

Figure 5:
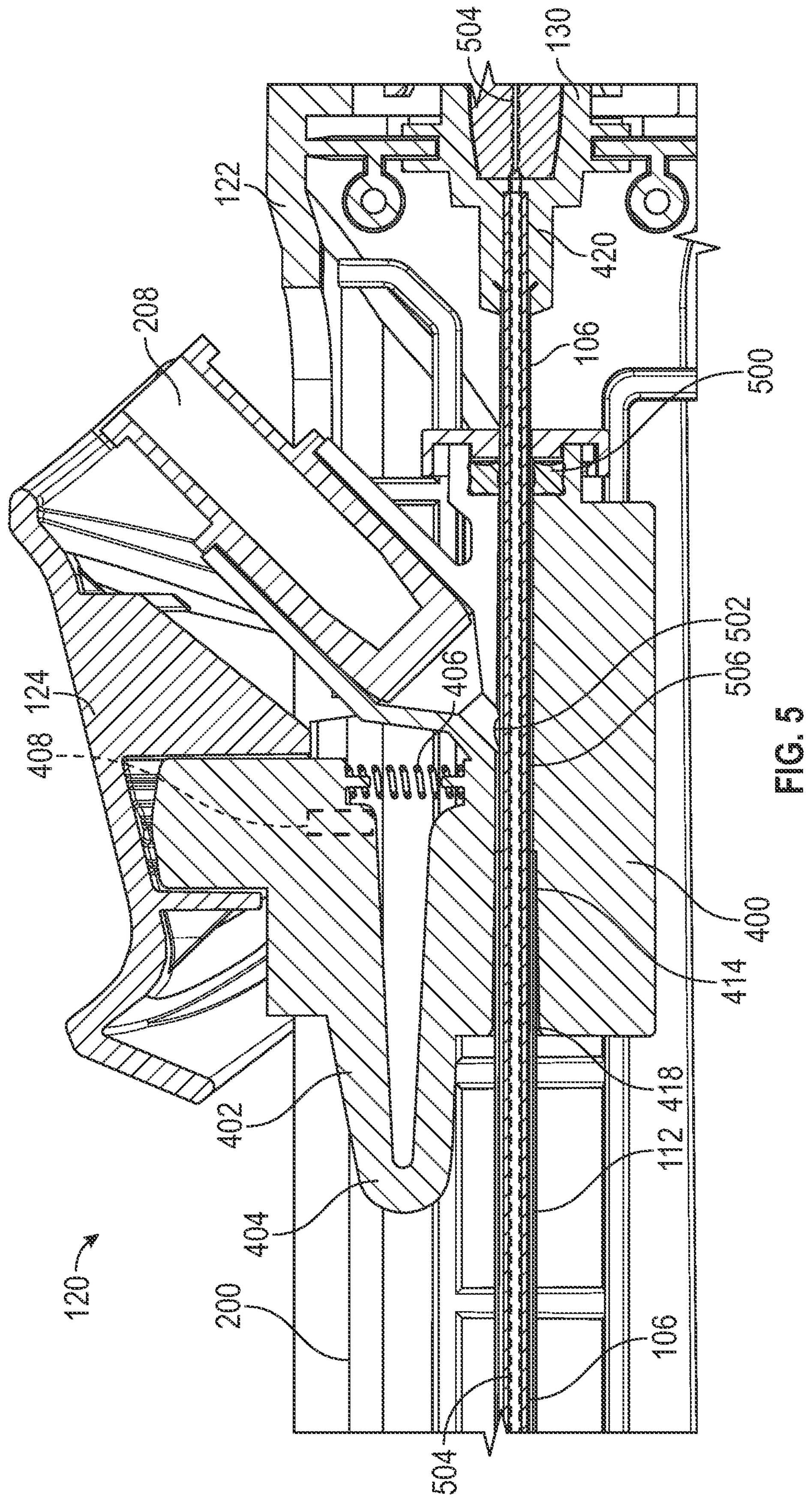
FIG. 5 is a detailed sectional view of one example of a sheath actuator of the manipulation controller of FIG. 1.

FIG. 5 is a cross sectional view of a portion of the manipulation controller 120. As shown in FIG. 5, the sheath actuator 124 is provided along the actuator track 200 of the controller housing 122. As further shown, a sheath catheter proximal portion 418 of the sheath shaft 112 is received in and coupled with the sheath actuator 124, for instance, at the sheath seat 414. The trumpet shaft 106 of the trumpet catheter 102 extends through a trumpet catheter passage 506 provided in the sheath actuator 124 and extends to another portion of the controller housing 122 including, for instance, the trumpet seat 420. The sheath actuator 124 and the sheath shaft 112 of the sheath catheter 110 are slidably or translationally moveable relative to the trumpet shaft 106. According, the sheath catheter 110 is slidable or trackable along the trumpet shaft 106 having the trumpet 104 (see FIGS. 1 and 3) to permit storage and deployment of the trumpet 104.

As further shown in FIG. 5 in dashed lines, one example of a capture catheter 504 extends through the manipulation controller 120. For instance, in this example, the capture catheter 504 (shown in dashed lines) extends through the catheter lock 130, the trumpet seat 420, the trumpet shaft 106 and the sheath actuator 124. The capture catheter 504, in this example, extends through the lumen of the trumpet shaft 106 and optionally extends through the trumpet 104 of the trumpet catheter 102.

Referring again to FIG. 5, the sheath actuator 124 is shown with the shuttle toggle 402 as an example of a manual operator of the sheath actuator 124, such as a depressible feature, button or the like of the sheath actuator 124. In one example, the sheath actuator 124 includes the anchor biasing element 404, such as a living hinge, configured to bias a portion of the sheath actuator 124 such as the anchor 408 (shown in dashed lines) toward a locked or seated configuration relative to one or more of the anchor sockets, such as the anchor sockets 410, 412 shown in FIGS. 4A and 4B. In another example, the sheath actuator 124 includes one or more other anchor biasing elements, such as the anchor biasing element 406 (e.g., a coiled spring or the like) coupled between the shuttle toggle 402 and the remainder of the sheath actuator 124 such as the actuator shuttle 400.

As further shown in FIG. 5, the flushing port 208 previously shown in FIG. 2B is, in one example, a component coupled with the sheath actuator 124. The flushing port 208 optionally includes a unidirectional valve such as a Luer defeatable valve that permits the introduction of fluids (e.g., flushing fluid, saline, thrombolytics or the like) through a flush channel 502 and into the trumpet catheter passage 506 provided within the sheath actuator 124. In one example, the trumpet catheter passage 506 permits the passage of the trumpet shaft 106 through the actuator shuttle 400, for instance, to seat within the trumpet seat 420. In another example, the trumpet catheter passage 506 is connected with the flushing port 208, for instance, with the flush channel 502 to permit the introduction of saline or other flushing fluids through the flushing port 208 to the space between the sheath shaft 112 and the trumpet shaft 106. Flushing of the volume between the sheath shaft 112 and the trumpet shaft 106 expels or evacuates one or more of particulate, air or the like therein prior to use of the thrombectomy assembly 100 within the vasculature. In an example, a flush gasket 500 is coupled with the sheath actuator 124 and extends around the trumpet shaft 106. With the flush gasket 500 present, flushing fluid introduced through the flushing port 208 is distally directed along the catheters 102, 110 instead of leaking from the sheath actuator 124, for instance, through the proximal portions of the actuator shuttle 400.

Referring to FIGS. 1, 2A and 2B, as previously described, the manipulation controller 120 is operated, in one example, to control the movement of the sheath catheter 110 relative to the trumpet catheter 102 and the deployable trumpet 104. For instance, as shown in FIG. 1, the sheath actuator 124 of the manipulation controller 120 is positioned in a retracted (proximal) position to correspondingly move the sheath actuator 110 and the associated sheath catheter 110 to reveal the trumpet 104 and permit its deployment into the deployed configuration shown in FIG. 1. As shown in FIGS. 4A and 4B, the sheath actuator 124 is, in one example, moveable relative to the manipulation controller 120, for instance, from the retracted position shown in FIGS. 4A and 4B to a an extended (distal) configuration, for instance, shown in one or more of the later figures provided herein including FIG. 9.

In operation, to transition the sheath catheter 110 between the retracted and extended configurations movement of the sheath actuator 124 is initiated, for instance, with translational movement of the actuator 124 relative to the remainder of the manipulation controller 120. Referring to FIG. 4B, in one example, the sheath actuator 124 is depressed, for instance to unseat one or more anchors 408 of the sheath actuator 124 relative to anchor sockets, such as the anchor socket 412 shown in FIG. 4B. Depression of the sheath actuator 124 overcomes bias provided by one or both of the anchor biasing elements 404, 406. Once depressed, the anchor 408 is misaligned with the anchor socket 412 and the sheath actuator 124 is readily moved relative to the manipulation controller 120 along the actuator track 200. In one example, a clinician, operator or the like manually handling the manipulation controller 120 uses thumb movement of the sheath actuator 124 to slide the sheath actuator 124 distally, for instance, toward a distal end of the manipulation controller 120.

Referring to FIG. 1, movement of the sheath actuator 124 moves the sheath catheter 110 coupled with the sheath actuator 124 and thereby positions the sheath catheter 110 over the trumpet 104 and compresses the trumpet 104 to a smaller profile, for instance, a profile that permits navigation of the thrombectomy assembly 100 through the vasculature. Continued movement of the sheath actuator 124 toward the distal portion of the manipulation controller 120, in one example, moves the anchor 408 into alignment with the anchor socket 410 (see FIG. 4B). Release of the sheath actuator 124 permits the elevation of the sheath actuator 124 such as the anchor 408 into the anchor socket 410 and holds the sheath actuator 124 and the sheath catheter 110 in the extended position relative to the trumpet 104 (e.g., in a stored configuration). This position of the sheath actuator 124 is affirmatively held, locked or the like with the sheath actuator 124, its one or more anchors 408 and anchor sockets 410 and thereby maintains the trumpet 104 in an affirmative stowed or stored configuration.

When deployment of the trumpet 104 is specified, the process of depressing the sheath actuator 124 and overcoming the bias of one or more of the anchor biasing elements 404, 406 is repeated and the sheath actuator 124, in this example, is moved proximally into the configuration shown in FIGS. 1 and 4B to translate the sheath catheter 110 relative to the trumpet catheter 102 and thereby reveal the trumpet 104 and permit its deployment.

Figure 6:
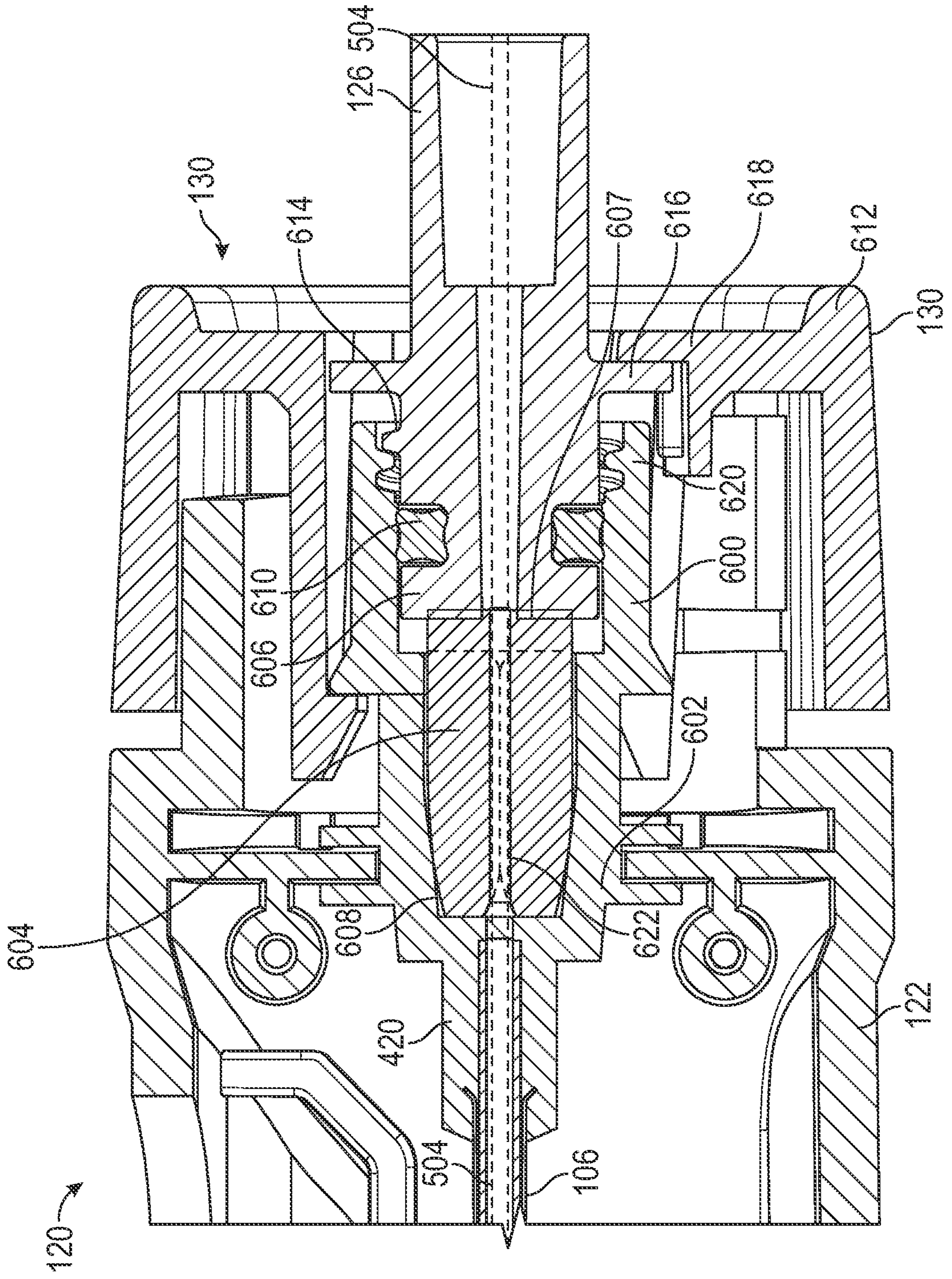
FIG. 6 is a detailed sectional view of one example of a catheter lock of the manipulation controller of FIG. 1.

FIG. 6 is a cross sectional view of a portion of the manipulation controller 120 including, for instance, the portion of the controller 120 having the catheter lock 130. As shown in FIG. 6, the catheter lock 130 includes one or more components that selectively permit or constrain motion of instruments (e.g., statically couple) coupled with the manipulation controller 120. As described herein, the catheter lock 130 in a locked configuration constrains motion of the instruments and instead permits consolidated movement of the thrombectomy assembly 100, for instance with manual (e.g., hand) manipulation of the manipulation controller 120. One example of an instrument is shown in FIG. 6, and includes the capture catheter 504.

The catheter lock 130, in this example, is shown coupled with the remainder of the controller housing 122. For instance, the catheter lock 130, in this example, includes a lock body 602 coupled with the remainder of the controller housing 122. The lock body 602 includes a collet seat 608 sized and shaped to receive a collet 604. The collet 604, in one example, includes a deformable member including, but not limited to, a deformable ring, gasket, elongate tubular gasket or the like. The collet 604 is shown with each of unlocked and locked configurations in FIG. 6. In the unlocked configuration, the collet 604 assumes the profile shown in solid lines in FIG. 6. For instance, the collet 604 has a greater length in comparison to a compressed configuration corresponding to the locked configuration. The compressed configuration is shown in dashed lines in FIG. 6 and shows the collet 604 with a shortened profile relative to the unlocked configuration and with a collet passage 622 compressed by the surrounding collet 604. As described herein, compression of the collet 604, for instance, including deformation into the collet passage 622, grasps one or more features extending through the collet passage 622, such as the capture catheter 504, and accordingly locks or maintains the capture catheter 504 in static coupling (e.g., constrains relative motion) with the remainder of the thrombectomy assembly 100.

As further shown in FIG. 6, in this example, the catheter lock 130 includes a collet driver 606 coupled with the remainder of the catheter lock 130. In one example, the collet driver 606 includes a driving face 607 or the like configured to engage with the collet 604. In combination the collet driver 606 and the collet 604 are one example of a lock mechanism 600. As described herein, movement of the collet driver 606, (e.g., caused, in one example, with rotation of the collet driver) moves the collet driver 606 into or biases the collet driver 606 toward the collet 604. The collet driver 606 compresses the collet 604 in a longitudinal fashion and precipitates compression of the collet 604 into the collet passage 622 to accordingly lock the catheter lock 130 and initiate static coupling with one or more instruments provided through the collet passage 622.

Optionally, a lock gasket 610 is provided with the collet driver 606 and coupled between the collet driver 606 and the lock body 602. The lock gasket 610 inhibits the passage of fluids such as body fluids, treatment fluids, flushing fluids or the like through the catheter lock 130 and minimizes leaks through the introduction port 126 and from the proximal portions of the manipulation controller 120.

In operation, the catheter lock 130, in one example, begins in an unlocked configuration, for instance, the configuration shown in FIG. 6 with solid lines. In such an example, the capture catheter 504 or other instrument provided through the collet passage 622 is permitted to move relative to the remainder of the manipulation controller 120. For instance, the capture catheter 504 is rotatable, translatable or the like relative to the controller housing 122 of the manipulation controller 120 as well as one or more of the other catheters, such as the trumpet catheter 102, sheath catheter 110 or the like associated with the manipulation controller 120.

Upon specification of the lock configuration, the operator, for instance, a clinician using the manipulation controller 120 grasps the lock actuator 612 coupled with the collet driver 606. As shown in FIGS. 2A and 2B, the catheter lock 130, in this example, is rotated. For instance, the lock actuator 612 is rotated to accordingly move the lock indicator 202 shown in FIG. 2A from the unlocked indicia 204 to the locked indicia 206 shown in FIG. 2B. As the lock actuator 612 is rotated in this manner, the collet driver 606 is rotated with the lock actuator 612, for instance, by way of an interference fit, keyed fitting, adhesives or the like. Rotation of the collet driver 606 engages the threaded interface 614 between the collet driver 606 and the lock body 602 and accordingly drives the collet driver 606 toward the collet 604. Continued rotation of the lock actuator 612 and the collet driver 606 longitudinally compresses the collet 604 into the configuration shown with dashed lines in FIG. 6. The longitudinal compression of the collet 604 correspondingly compresses the collet 604 around the collet passage 622 and the deformed collet 604 grasps one or more components provided through the collet passage 622.

In an example, the capture catheter 504 is the instrument extending through the collet passage 622 and the collet 604 in the locked configuration compresses around the capture catheter 504 and affirmatively engages with the capture catheter 504 to thereby statically couple the capture catheter 504 with the remainder of the thrombectomy assembly 100. In the locked configuration, the catheter lock 130 permits unitary or consolidated movement of the thrombectomy assembly. For instance, movement of the manipulation controller 120 (rotation, translation or the like) accordingly causes corresponding movement of the components associated with the manipulation controller 120 including the locked capture catheter 504.

When unlocking of the capture catheter 504 or other instrument is specified the lock actuator 612 is rotated in a second opposed direction and the collet driver 606 having the threaded interface 614 is accordingly retracted relative to the locked configuration. The previously deformed collet 604 relaxes in a longitudinal manner and the collet passage 622 expands as the collet 604 retracts away toward the configuration of the collet passage 622 shown in solid lines. The capture catheter 504 or other instrument provided in the collet passage 622 is freed to move translationally, rotationally or the like relative to the remainder of the thrombectomy assembly 100.

In another example, the catheter lock 130 includes one or more of an unlocked flange 618 and a locked flange 620. In various examples, the locked flange 618 limits the motion of the collet driver 606 to minimize over compression of the deformable collet 504 like. The unlocked flange 618, in another example, prevents or minimizes the likelihood of decoupling of the collet driver 606 from the remainder of the catheter lock 130. As shown in FIG. 6, the collet driver 606 optionally includes a driver flange 616 that is moveable between each of the locked flange 620 and the unlocked flange 618. In the unlocked configuration shown in solid lines in FIG. 6, the driver flange 616 is proximate to or coupled along the unlocked flange 618 and further movement of the collet driver 606 in a proximal fashion (to the right of the page) is prohibited. Conversely, with the catheter lock 130 in the locked configuration, the driver flange 616 is moved in a distal manner and is coupled along the lock flange 620 corresponding to specified deformation of the collet 604 to statically couple one or more instruments provided in the collet passage 622. The lock flange 620 further prevents additional deflection or deformation of the collet 604, for instance, with continued driving of the collet driver 606.

Figure 7:
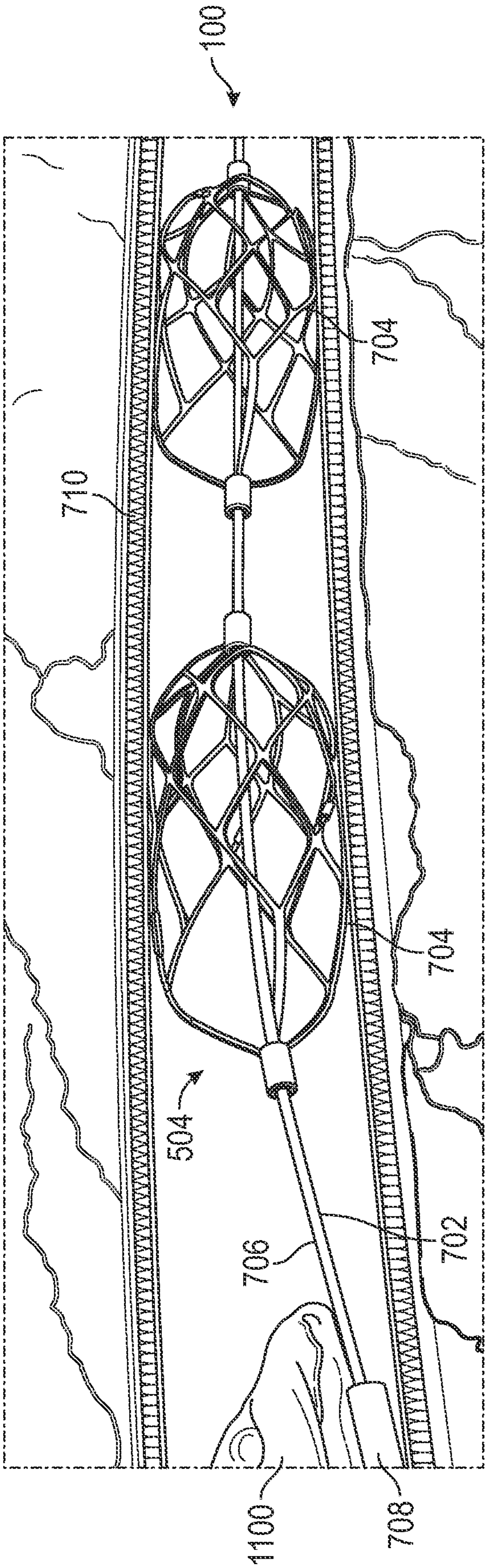
FIG. 7 is a perspective view of one example of a deployed capture catheter of a thrombectomy assembly.

FIG. 7 is a perspective view of one example of a thrombectomy assembly 100 in an initial configuration of a thrombectomy procedure to capture thrombus 1100 including, but not limited to, thrombus, clot, particulate or the like in a vessel 710. As shown in FIG. 7, one example of a capture catheter 504 is provided in a deployed configuration, for instance, with a capture catheter distal portion 706 having deployable cages 704 in deployed configurations. As shown the deployable cages 704 are navigated past the thrombus 1100, and positioned distal to the thrombus 1100. In an example, the capture catheter 504 is navigated (with the cages 704 stored) through a procedure sheath 800, shown in FIG. 8, to the location of interest.

As further shown in FIG. 7, the capture catheter 504 including its capture shaft 702 are, in one example, delivered through a capture sheath 708. In one example, the capture sheath 708 and capture shaft 702 including the deployable cages 704 thereon are navigated through the vasculature into the vessel 710, for instance along a guidewire, the procedural sheath 800 or the like. The capture catheter 504 is, in another example, navigated distally beyond a thrombus 1100 provided in the vessel 710. After delivery of the capture catheter 504 distally relative to the thrombus 1100, the capture sheath 708 is, in one example, withdrawn thereby allowing the deployable cages 704 to expand into a deployed configuration relative to the capture shaft 702. In one example, the deployable cages 704 deploy and engage with the walls of the vessel 710.

Figure 8:
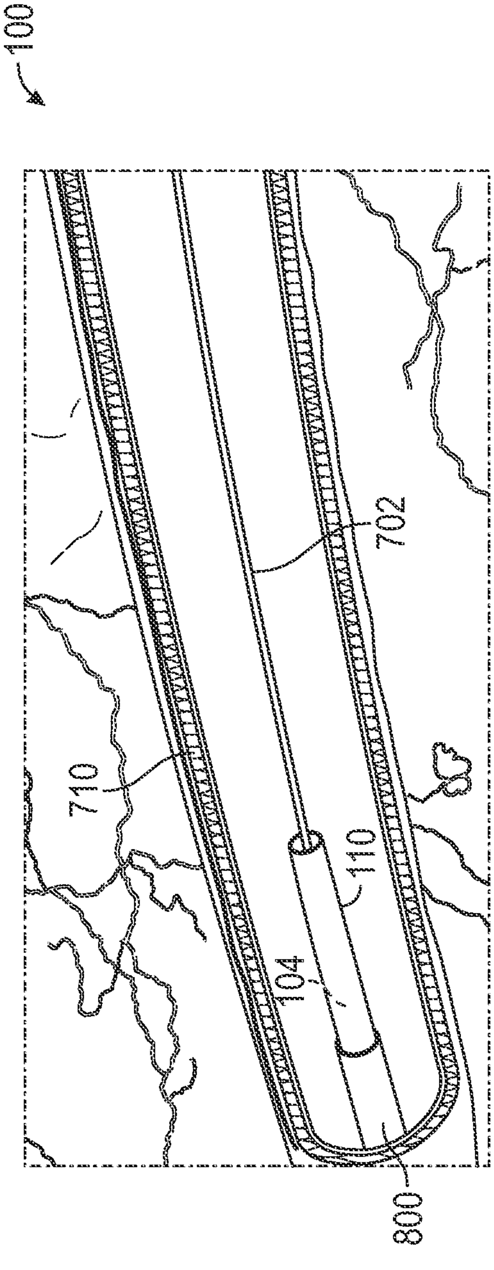
FIG. 8 is a perspective view of one example of deployment of a sheath catheter and trumpet.

Referring now to FIG. 8, another portion of the thrombectomy assembly 100 is shown within the vessel 710. The capture shaft 702 of the capture catheter 504 is shown again, and extends from the sheath catheter 110 and a procedure sheath 800. The thrombus 1100 and deployable cages 704 previously shown in FIG. 7 are distal relative to the view shown in FIG. 8 (e.g., to the right on the page). The procedure sheath 800 in some examples extends from a hub (shown in FIG. 14) to a distal end located proximate to a location of interest, for instance having thrombus 1100. The procedure sheath 800 is, in one example, shorter than each of the capture catheter 504, trumpet catheter 102, sheath catheter 110. For instance, the hub of the procedure sheath 800 is distal to the manipulation controller 120 (having the trumpet and sheath catheters 102, 110) and the capture shaft 702 of the capture catheter extends through the hub. The distal end of the procedure sheath 800 is proximal to the deployed trumpet 104 and deployable cages 704 (when deployed).

As shown in FIG. 8, the sheath catheter 110 is navigated through the procedure sheath 800 to the location of interest and extends along the capture shaft 702. The sheath catheter 110 shown in FIG. 8 corresponds to the sheath catheter 110 shown previously and described with regard to FIGS. 1, 2A and 2B and is coupled with the manipulation controller 120. In one example, the trumpet catheter 102 shown, for instance, in FIG. 1 and further shown in FIG. 3, is provided within the sheath catheter 110 and both the trumpet and sheath catheters 102, 110 are navigated through the vessel 710 with manipulation of the manipulation controller 120. In FIG. 8, the trumpet 104 of the trumpet catheter 102 is concealed within the sheath catheter 110. The capture shaft 702 of the capture catheter 504 is slidably received within the trumpet lumen 300 of the trumpet catheter 102. The trumpet catheter 102 is, in turn, received within the sheath lumen 302 of the sheath catheter 110 shown, for instance, in FIG. 8 and further shown in FIG. 3.

Figure 9:
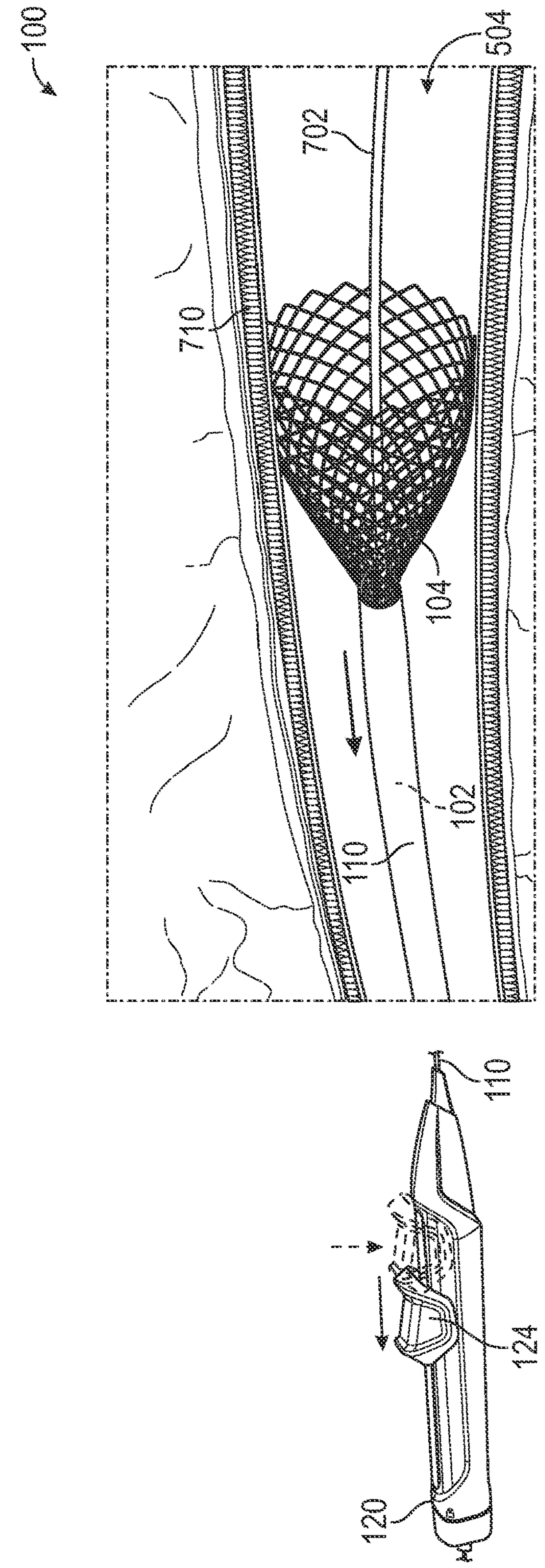
FIG. 9 is a perspective view of one example of deployment of a trumpet with the manipulation controller of FIG. 1.

Referring now to FIG. 9, the manipulation controller 120 is shown toward the left of the perspective view of the vessel 710. In this stage of the thrombectomy procedure, the thrombectomy assembly 100 is operated to deploy the trumpet 104 within the vessel 710. As previously described, the capture catheter 504, including its deployable cages 704, are distally positioned relative to the trumpet 104, and the thrombus 1100 is interposed between the trumpet 104 and the deployable cages 704.

In operation, the sheath actuator 124 of the manipulation controller 120 is actuated to reveal the trumpet 104. In an example, the sheath actuator 124 is initially depressed, for instance, as shown with the dashed arrow and dashed profile of the sheath actuator 124. The depression of the sheath actuator 124 unseats one or more anchors 408 relative to the anchor socket 410, for instance, provided along the actuator track 200 as shown in FIG. 4B. With the anchor 408 unseated, the sheath actuator 124 is permitted to move along the actuator track 200, and as shown in FIG. 9 is moved proximately (indicated with the solid arrow).

As previously described, the trumpet catheter 102 is, in one example, coupled with a corresponding portion of the manipulation controller 120. In one example, the trumpet catheter 102 is held static relative to the sheath actuator 110 by way of seating of the trumpet catheter at a trumpet seat 420, for instance, shown in FIG. 5. Movement of the sheath catheter 110 relative to the static trumpet catheter 102 reveals the trumpet 104. Movement of the sheath actuator 124 (shown with the solid arrow) moves the sheath catheter 110 coupled to the sheath actuator 124 and accordingly withdraws the sheath catheter 110 relative to the trumpet 104 as shown in the right view. Revelation of the trumpet 104 permits its deployment and accordingly the trumpet 104 gradually deploys from proximate the capture shaft 702 to an intimately engaged position with the vessel 710.

Figure 10:
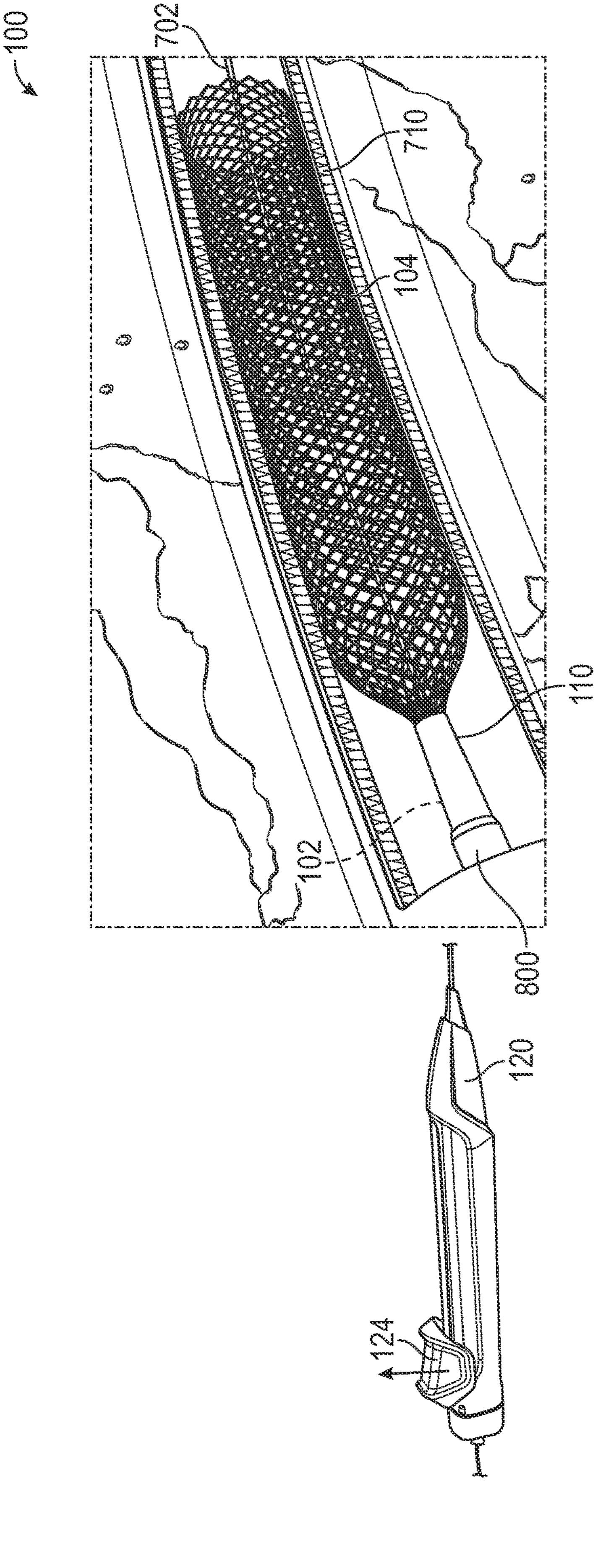
FIG. 10 is a perspective view of another example of deployment of the trumpet with the manipulation controller of FIG. 1.

Referring now to FIG. 10, proximal movement of the sheath actuator 124 is continued, as shown in the left view, to further retract the sheath catheter 110 relative to the trumpet 104. Additional length of the trumpet 104 is revealed with the sheath catheter 110 retraction and permits the continued deployment of the trumpet 104. In one example, the sheath actuator 124 is moved into a position shown in FIG. 10, for instance, with the sheath actuator 124 provided proximate to an end of the actuator track 200 previously shown in FIGS. 4A and 4B. As previously described in an example, the sheath actuator 124 includes one or more anchors 408 (see FIG. 4B). With the sheath actuator 124 retracted in the position shown in FIG. 10, the sheath actuator 124, including the one or more anchors 408, is permitted to elevate and seat the anchor 408 within a corresponding anchor socket 412 of the manipulation controller 120. The one or more biasing elements, such as the biasing elements 404, 406 or the like, bias a portion of the sheath actuator 124, such as the sheath toggle 402 to position the one or more anchors 408 within the one or more anchor sockets 412.

Coupling of the one or more anchors 408 with the one or more anchor sockets 412 statically couples the sheath actuator 124 and its associated sheath catheter 110 with the manipulation controller 120. Accordingly the sheath catheter 110 is statically retained in the retracted position shown in FIG. 10 relative to the trumpet 104 of the trumpet catheter 102. Accordingly, in the configuration with the sheath actuator 124 having its anchor 408 received within one or more of the anchor sockets 410, 412 movement of the manipulation controller 120 including, for instance, rotation, translation or the like is transmitted to each of the sheath catheter 110 and the trumpet catheter 102 (each statically coupled with the controller 120) to thereby consolidate movement of each of these components with the manipulation controller 120.

Figure 11:
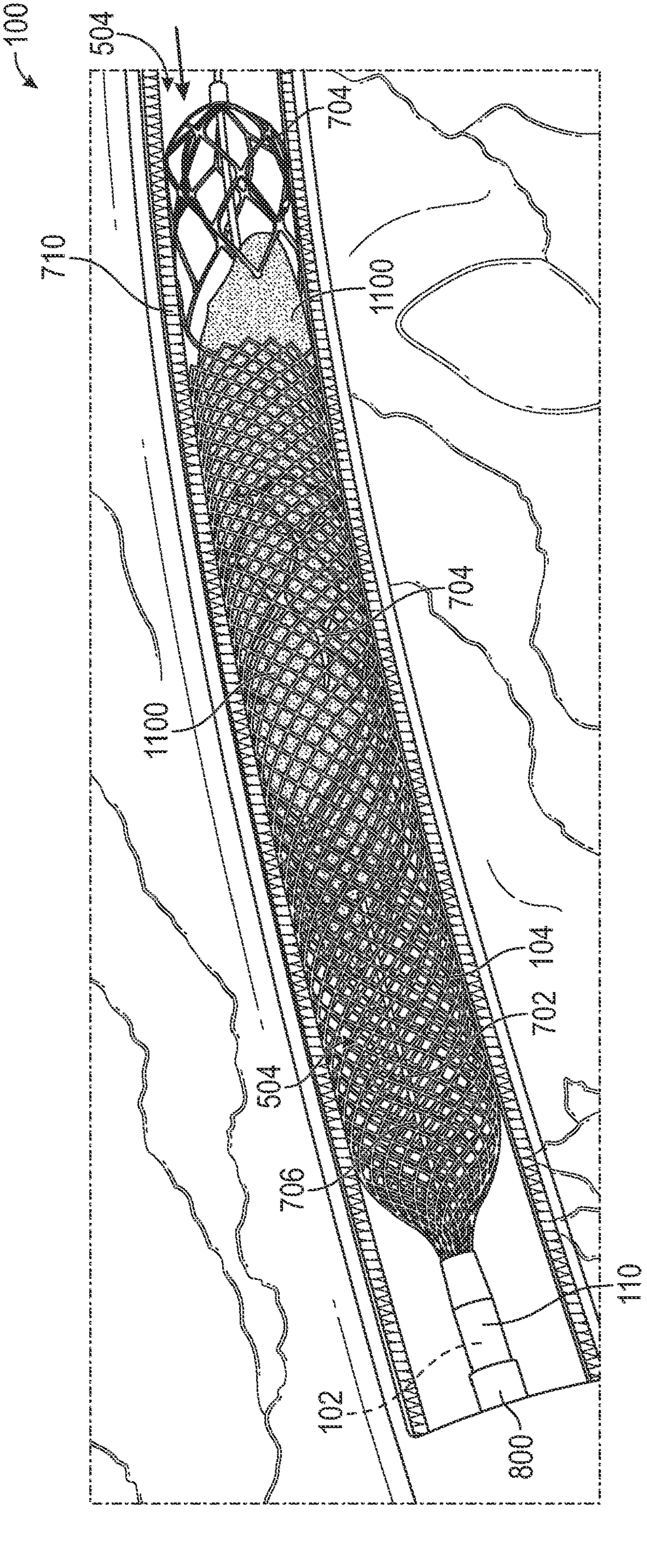
FIG. 11 is a perspective view of one example of the thrombectomy assembly capturing thrombus.

FIG. 11 is another perspective view of the thrombectomy assembly 100 in a capture configuration. In this example, the capture catheter 504, including the deployable cages 704, is withdrawn proximally relative to the trumpet 104 in its deployed configuration. The thrombus 1100 (e.g., thrombus, clot, particulate or the like) within the vessel 710 is captured between the trumpet 104 and the deployable cages 704 and pulled into the trumpet 104 to provide a nesting capture configuration with the trumpet 104 extending over the deployable cages 704 and the deployable cages extending over the thrombus 1100. The cooperative capture of the thrombus 1100 with each of the deployable cages 704 and the trumpet 104 minimizes the separation of particulate from the thrombus 1100 and enhances the capture of the thrombus, for instance, for retraction through the procedure sheath 800.

In one example, to initiate the capture of the thrombus 1100 within the deployable cages 704, the deployable cages 704 and the capture catheter 504 are moved relative to the trumpet catheter 102 including the trumpet 104. For instance, the capture catheter 504 extending through the introduction port 126 shown in FIG. 6 is drawn proximally relative to the manipulation controller 122. The deployable cages 704 coupled with the capture catheter 504 are accordingly moved proximally relative to the remainder of the thrombectomy assembly 100 including the manipulation controller 122, the trumpet shaft 102, the trumpet 104 and the sheath catheter 110. The relative movement moves the deployable cages 704 into engagement with the thrombus 1100, captures the thrombus 1100 within the cages, and moves the deployable cages 704 and captured thrombus 1100 into the trumpet 104.

Figure 12:
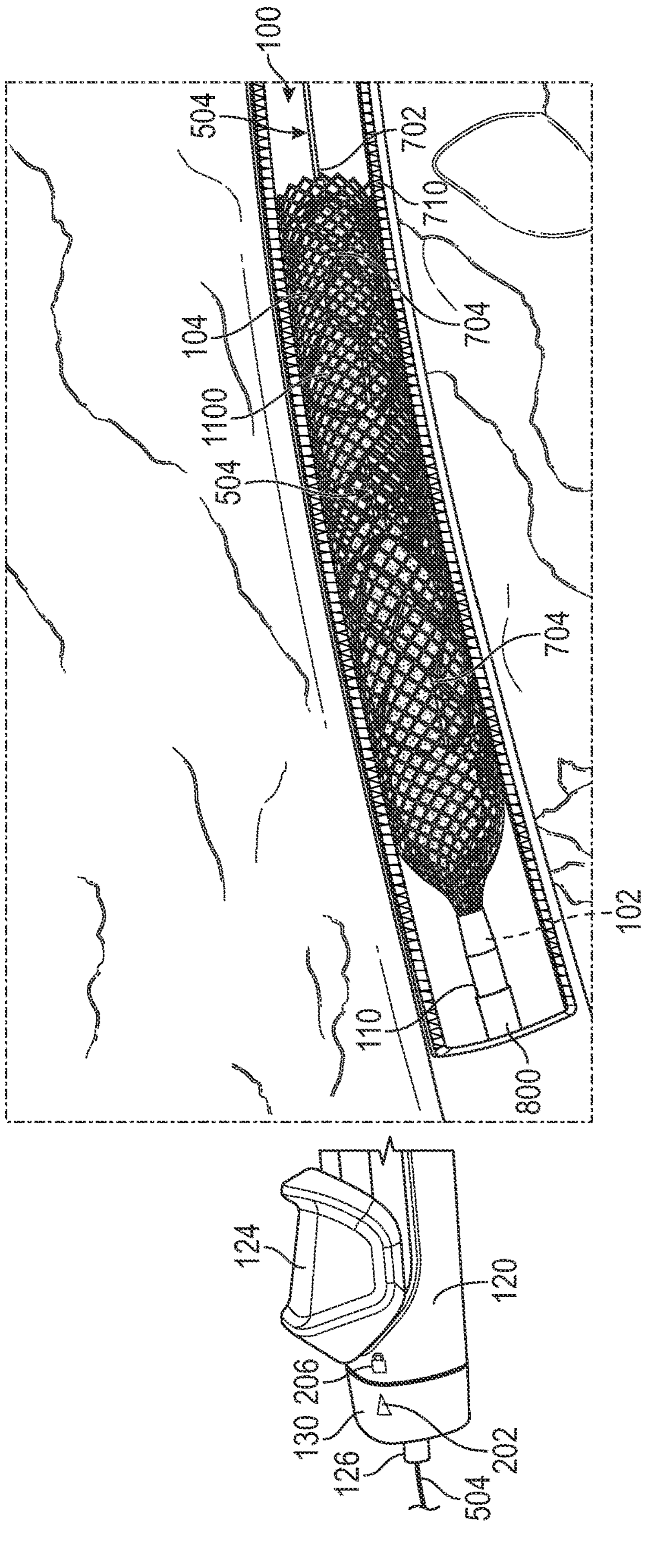
FIG. 12 is a perspective view of one example of actuation of a catheter lock.

In the configuration shown in FIG. 11, each of the trumpet catheter 102, the sheath catheter 110 and the capture catheter 504 extend distally from the manipulation controller 120 to the location of interest within the vessel 710, for instance, the location having the thrombus 1100. In this configuration, with the deployable cages 704 pulled into the trumpet 104, the capture catheter 504 is moveable relative to the sheath catheter 110 and the trumpet catheter 102 because the catheter lock 130 is in an unlocked configuration and the capture catheter is statically decoupled (also referred to as dynamically coupled) with the manipulation controller 120. As shown in FIG. 12, the deployable cages 704, the thrombus 1100 are further retracted into the trumpet 104 (e.g., moved relative to the trumpet catheter 102 and the sheath catheter 110).

FIG. 12 shows the thrombus 1100 in a fully captured configuration, for instance, within the deployable cages 704, and with the cages 704 within the trumpet 104. As provided in the left view of FIG. 12, the catheter lock 130 of the manipulation controller 120 is actuated to transition the catheter lock from an unlocked configuration (e.g., statically decoupled, dynamically coupled, permits movement) to a locked configuration (e.g., statically coupled, constrains relative movement). In this example the catheter lock 130 is rotated as shown in FIGS. 2A, B to move the locking indicator 202 (previously shown in FIG. 2A) toward the locked indicia 206 shown in FIG. 2B. Referring to FIG. 6, actuation of the catheter lock 130 deforms the collet 604 from the configuration shown in solid lines to the compressed configuration or locking configuration shown in dashed lines. The collet 604 compresses around one or more components extending through the collet passage 622. In this example, with the capture catheter 504 having the capture shaft 702 extending through the collet 604, the collet 604 grasps the capture shaft 702 and accordingly locks (e.g., statically couples) the capture shaft and the remainder of the capture catheter 504 with the other components of the thrombectomy assembly 100 including, but not limited to, the trumpet catheter 102, the sheath catheter 110, the trumpet 104 and the manipulation controller 120. In the locked configuration, actuation of the manipulation controller including manual (hand) operation by the clinician, operator or the like transmits corresponding movement to each of the components of the thrombectomy assembly 100 including the locked capture catheter 504. For instance, proximal movement of the manipulation controller 120 moves each of the trumpet catheter 102, the sheath catheter 110 as well as the trumpet 104, the capture catheter 504, deployable cages 704 and the thrombus 1100 therein. The trumpet 104, cages 704 and the thrombus 1100 are moved proximally together toward the procedure sheath 800 and the associated catheters, such as the trumpet catheter 102, capture catheter 504 or the like are moved proximally together within the procedure sheath 800.

Figure 13:
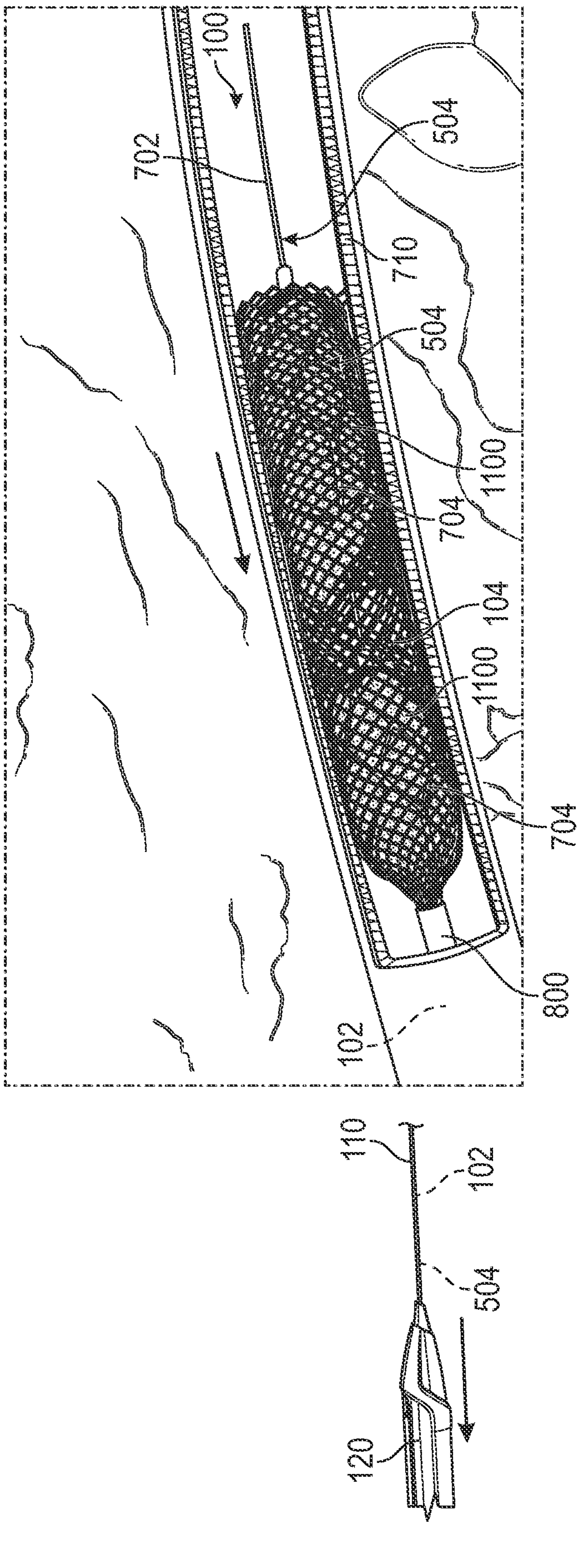
FIG. 13 is a perspective view of one example of retraction of the thrombectomy assembly into a procedure sheath with the manipulation controller.

As shown in FIG. 13, continued movement of the manipulation controller 120, for instance, in the proximal direction shown in FIG. 13, draws the trumpet 102, the deployable cages 704 as well as the captured thrombus 1100 into the procedure sheath 800. A distal end of the procedure sheath 800 (as shown in FIG. 13) is proximate to these components and positioned proximally. The proximal coordinated movement of each of these components together minimizes shearing forces between each of the components and accordingly assists in maintaining the thrombus 1100 as a collective mass and minimizes (decreases, eliminates or the like) the generation of particulate or the like that is separated from the thrombus, cages 704 or trumpet 104 and left in the vessel 710. Instead, each of the trumpet 104, the deployable cages 704 and the thrombus 1100 are drawn as a single unit moving together (e.g., consolidated movement) into the procedure sheath 800 while their associated catheters are proximally withdrawn through the procedure sheath. The trumpet 104, deployable cages 704 and the thrombus 1100 are compressed as these components are drawn into the procedure sheath 800 to facilitate the retraction of the thrombectomy assembly 100 including the thrombus 1100 through the assembly as shown in FIG. 14.

Figure 14:
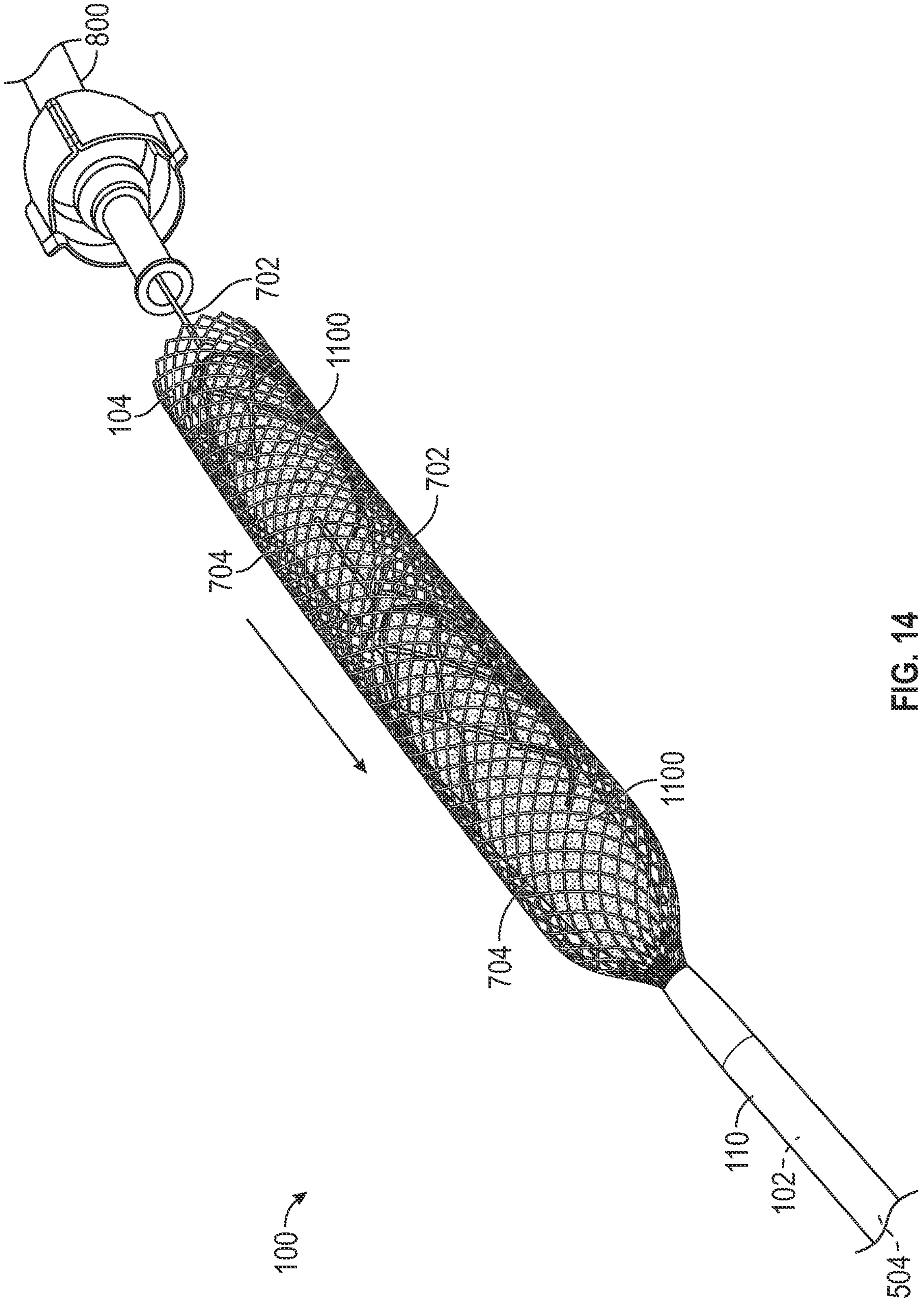
FIG. 14 is a perspective view of one example of withdrawal of the thrombectomy assembly 100 from the procedure sheath of FIG. 13.

FIG. 14 shows another perspective view of the thrombectomy assembly 100. In this example, a distal end of the procedure sheath 800 is shown and the captured thrombus 1100 is withdrawn from the procedure sheath 800. In this example, the manipulation controller 120 is in the locked configuration and accordingly each of the capture catheter 504, the trumpet catheter 102, the sheath catheter 110 and their associated components as well as the captured thrombus 1100 are moved proximally together and in a consolidated manner as shown with the arrow in FIG. 14 relative to the procedure sheath 800. Movement of each of these components as a collective assembly, as previously described, minimizes shearing between the components and accordingly minimizes the generation of particulate from the thrombus 1100. Further, the operator, clinician or the like is permitted, in one example with one hand, to grasp the manipulation controller 120 in the locked configuration and retract each of the components of the thrombectomy assembly 100 in a collective fashion and withdraw all of these components together through the procedure sheath 800.

In one example, after retraction of the thrombus 1100 from the procedure sheath 800, the manipulation controller 120 is further actuated, for instance, to release the locking configuration of the catheter lock 130 and permit relative movement between the capture catheter 504 and the remainder of the thrombectomy assembly, for instance, to facilitate decoupling of the capture catheter 504, cleaning of thrombus 1100 from the assembly 100 components or the like.

VARIOUS NOTES AND ASPECTS

Aspect 1 can include subject matter such as a thrombectomy assembly comprising: a trumpet catheter including a trumpet lumen configured to receive a capture catheter therein, the trumpet catheter having a deployable trumpet proximate to a trumpet catheter distal portion; and a manipulation controller coupled with the trumpet catheter proximate to a trumpet catheter proximal portion, the manipulation controller includes: a controller housing coupled with the trumpet catheter; a catheter lock coupled with the controller housing, the catheter lock includes: a deformable collet having a collet passage configured to receive the capture catheter therein, the collet passage aligned with the trumpet lumen; and a collet driver coupled with the deformable collet; and wherein the catheter lock includes locked and unlocked configurations: in the locked configuration the collet driver compresses the deformable collet, and the deformable collet compresses around the capture catheter and statically couples the capture catheter to the controller housing; and in the unlocked configuration the collet driver is relaxed from the deformable collet relative to the locked configuration and the deformable collet expands around the capture catheter and statically decouples the capture catheter relative to the controller housing.

Aspect 2 can include, or can optionally be combined with the subject matter of Aspect 1, to optionally include the capture catheter.

Aspect 3 can include, or can optionally be combined with the subject matter of one or any combination of Aspects 1 or 2 to optionally include wherein the capture catheter includes a capture shaft and at least one deployable cage coupled with the capture shaft.

Aspect 4 can include, or can optionally be combined with the subject matter of one or any combination of Aspects 1-3 to optionally include wherein in the unlocked configuration at least longitudinal movement of the controller housing moves at least the trumpet catheter relative to the capture catheter; and in the locked configuration at least longitudinal movement of the controller housing moves the trumpet catheter and the capture catheter together.

Aspect 5 can include, or can optionally be combined with the subject matter of one or any combination of Aspects 1-4 to optionally include wherein rotation of the catheter lock in a first direction is configured to initiate the locked configuration; and rotation of the catheter lock in a second direction is configured to initiate the unlocked configuration.

Aspect 6 can include, or can optionally be combined with the subject matter of Aspects 1-5 to optionally include wherein the catheter lock includes a lock body having a collet seat, and the deformable collet is received in the collet seat.

Aspect 7 can include, or can optionally be combined with the subject matter of Aspects 1-6 to optionally include wherein the collet driver is movably coupled with the lock body.

Aspect 8 can include, or can optionally be combined with the subject matter of Aspects 1-7 to optionally include wherein the collet driver movably coupled with the lock body includes the collet driver rotatably coupled with the lock body with a threaded interface.

Aspect 9 can include, or can optionally be combined with the subject matter of Aspects 1-8 to optionally include wherein the lock body includes a trumpet seat, and the trumpet catheter is received in the trumpet seat.

Aspect 10 can include, or can optionally be combined with the subject matter of Aspects 1-9 to optionally include a sheath catheter with a sheath lumen, wherein the trumpet catheter is received in the sheath lumen; wherein the manipulation controller includes a sheath actuator movably coupled with the controller housing, and the sheath actuator is configured to move the sheath catheter relative to the trumpet catheter and transition the deployable trumpet between a stored configuration with the deployable trump compressed and a deployed configuration with the deployable trump expanded.

Aspect 11 can include, or can optionally be combined with the subject matter of Aspects 1-10 to optionally include a thrombectomy assembly comprising: a sheath catheter including a sheath lumen; a trumpet catheter including a trumpet lumen, the trumpet catheter having a deployable trumpet proximate to a trumpet catheter distal portion, the trumpet catheter is received in the sheath lumen; a manipulation controller configured to actuate the sheath catheter and the trumpet catheter, the manipulation controller includes: a controller housing coupled with the trumpet catheter; and a sheath actuator coupled with the sheath catheter, the sheath actuator is movable relative to the controller housing and configured to move the sheath catheter relative to the trumpet catheter; and wherein the deployable trumpet includes deployed and stored configurations: in the stored configuration the sheath actuator is in a first position relative to the controller housing, and the sheath catheter extends over the deployable trumpet; and in the deployed configuration the sheath actuator is in a second position relative to the controller housing, the sheath catheter is retracted from the deployable trumpet, and the deployable trumpet is expanded relative to the stored configuration.

Aspect 12 can include, or can optionally be combined with the subject matter of Aspects 1-11 to optionally include wherein the controller housing includes a trumpet seat, and the trumpet seat anchors a trumpet catheter proximal portion of the trumpet catheter with the controller housing.

Aspect 13 can include, or can optionally be combined with the subject matter of Aspects 1-12 to optionally include wherein the sheath actuator includes a sheath seat, and the sheath seat anchors a sheath catheter proximal portion of the sheath catheter, and the sheath actuator and sheath catheter are movable together relative to the trumpet catheter.

Aspect 14 can include, or can optionally be combined with the subject matter of Aspects 1-13 to optionally include wherein the sheath actuator includes an actuator shuttle movably coupled along an actuator track of the controller housing.

Aspect 15 can include, or can optionally be combined with the subject matter of Aspects 1-14 to optionally include wherein the actuator shuttle includes a trumpet catheter passage, the trumpet catheter is received in the trumpet catheter passage, and the actuator shuttle is slidably coupled with the trumpet catheter.

Aspect 16 can include, or can optionally be combined with the subject matter of Aspects 1-15 to optionally include wherein the sheath actuator includes at least one anchor, and the controller housing includes at least one anchor socket.

Aspect 17 can include, or can optionally be combined with the subject matter of Aspects 1-16 to optionally include wherein the at least one anchor socket includes a retracted anchor socket, and in the deployed configuration the at least one anchor is received in the retracted anchor socket.

Aspect 18 can include, or can optionally be combined with the subject matter of Aspects 1-17 to optionally include wherein the at least one anchor socket includes an extended anchor socket, and in the stored configuration the at least one anchor is received in the extended anchor socket.

Aspect 19 can include, or can optionally be combined with the subject matter of Aspects 1-18 to optionally include wherein sheath actuator includes at least one anchor biasing element coupled with the at least one anchor, the at least one anchor biasing element is configured to bias the anchor toward the at least one anchor socket.

Aspect 20 can include, or can optionally be combined with the subject matter of Aspects 1-19 to optionally include wherein the manipulation controller includes a catheter lock coupled with the controller housing, the catheter lock includes: a deformable collet having a collet passage configured to receive a capture catheter therein, the collet passage aligned with the trumpet lumen; and a collet driver coupled with the deformable collet.

Aspect 21 can include, or can optionally be combined with the subject matter of Aspects 1-20 to optionally include wherein the catheter lock includes locked and unlocked configurations: in the locked configuration the collet driver longitudinally compresses the deformable collet, and the deformable collet compresses around the capture catheter and statically couples the capture catheter to the controller housing; and in the unlocked configuration the collet driver is relaxed from the deformable collet relative to the locked configuration and the deformable collet expands around the capture catheter and statically decouples the capture catheter relative to the controller housing.

Aspect 22 can include, or can optionally be combined with the subject matter of Aspects 1-21 to optionally include comprising the capture catheter.

Aspect 23 can include, or can optionally be combined with the subject matter of Aspects 1-22 to optionally include a thrombectomy assembly comprising: a sheath catheter including a sheath lumen; a trumpet catheter including a trumpet lumen configured to receive a capture catheter therein, the trumpet catheter having a deployable trumpet, and the trumpet catheter is received in the sheath lumen; and a manipulation controller coupled with the trumpet catheter and the sheath catheter, the manipulation controller includes: a controller housing coupled with the trumpet catheter; a sheath actuator coupled with the sheath catheter, the sheath actuator is movably coupled with the controller housing; and a catheter lock coupled with the controller housing, the catheter lock includes a deformable collet having a collet passage configured to receive the capture catheter therein, the collet passage aligned with the trumpet lumen; wherein the sheath actuator is configured to move the sheath catheter between a deployed configuration with the sheath actuator retracted from the deployable trumpet and a stored configuration with the sheath actuator covering the deployable trumpet; and wherein the deformable collet is configured to transition between a locked configuration with the deformable collet compressed around the capture catheter and the controller housing is statically coupled to the capture catheter and an unlocked configuration with the deformable collet expanded around the capture catheter and the controller housing is statically decoupled relative to the capture catheter.

Aspect 24 can include, or can optionally be combined with the subject matter of Aspects 1-23 to optionally include wherein the sheath actuator includes a sheath seat, and the sheath seat anchors a sheath catheter proximal portion of the sheath catheter, and the sheath actuator and sheath catheter are movable together relative to the trumpet catheter.

Aspect 25 can include, or can optionally be combined with the subject matter of Aspects 1-24 to optionally include wherein the sheath actuator includes a trumpet catheter passage, the trumpet catheter is received in the trumpet catheter passage, and the sheath actuator is slidably coupled with the trumpet catheter.

Aspect 26 can include, or can optionally be combined with the subject matter of Aspects 1-25 to optionally include wherein the sheath actuator includes at least one anchor, and the controller housing includes at least one anchor socket.

Aspect 27 can include, or can optionally be combined with the subject matter of Aspects 1-26 to optionally include wherein the at least one anchor socket includes: a retracted anchor socket, and in the deployed configuration the at least one anchor is received in the retracted anchor socket; and an extended anchor socket, and in the stored configuration the at least one anchor is received in the extended anchor socket.

Aspect 28 can include, or can optionally be combined with the subject matter of Aspects 1-27 to optionally include wherein sheath actuator includes at least one anchor biasing element coupled with the at least one anchor, the at least one anchor biasing element is configured to bias the anchor toward the at least one anchor socket.

Aspect 29 can include, or can optionally be combined with the subject matter of Aspects 1-28 to optionally include wherein in the unlocked configuration at least longitudinal movement of the controller housing moves the trumpet catheter and the sheath catheter relative to the capture catheter; and in the locked configuration at least longitudinal movement of the controller housing moves the trumpet catheter, the sheath and catheter and the capture catheter together.

Aspect 30 can include, or can optionally be combined with the subject matter of Aspects 1-29 to optionally include wherein rotation of the catheter lock in rotation a first direction is configured to initiate the locked configuration; and of the catheter lock in a second direction is configured to initiate the unlocked configuration.

Aspect 31 can include, or can optionally be combined with the subject matter of Aspects 1-30 to optionally include wherein the catheter lock includes collet driver movably coupled with the deformable collet.

Aspect 32 can include, or can optionally be combined with the subject matter of Aspects 1-31 to optionally include wherein in the locked configuration the collet driver longitudinally compresses the deformable collet, and the deformable collet radially compresses around the capture catheter according to the longitudinal compression; and in the unlocked configuration the collet driver is relaxed from the deformable collet relative to the locked configuration, and the deformable collet radially relaxes from the capture catheter according to the relaxing of the collet driver.

Aspect 33 can include, or can optionally be combined with the subject matter of Aspects 1-32 to optionally include the capture catheter.

Aspect 34 can include, or can optionally be combined with the subject matter of Aspects 1-33 to optionally include wherein the capture catheter includes a capture shaft and at least one deployable cage coupled with the capture shaft.

Each of these non-limiting aspects can stand on its own, or can be combined in various permutations or combinations with one or more of the other aspects.

The above description includes references to the accompanying drawings, which form a part of the detailed description. The drawings show, by way of illustration, specific embodiments in which the invention can be practiced. These embodiments are also referred to herein as "aspects" or "examples." Such aspects or example can include elements in addition to those shown or described. However, the present inventors also contemplate aspects or examples in which only those elements shown or described are provided. Moreover, the present inventors also contemplate aspects or examples using any combination or permutation of those elements shown or described (or one or more features thereof), either with respect to a particular aspects or examples (or one or more features thereof), or with respect to other Aspects (or one or more features thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described aspects or examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as aspects, examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A thrombectomy assembly comprising:

a trumpet catheter including a trumpet lumen configured to receive a capture catheter therein, the trumpet catheter having a deployable trumpet proximate to a trumpet catheter distal portion; and a manipulation controller coupled with the trumpet catheter proximate to a trumpet catheter proximal portion, the manipulation controller includes:

a controller housing coupled with the trumpet catheter;

a catheter lock coupled with the controller housing, the catheter lock includes:

a deformable collet having a collet passage configured to receive the capture catheter therein, the collet passage aligned with the trumpet lumen; and a collet driver coupled with the deformable collet; and wherein the catheter lock includes locked and unlocked configurations:

in the locked configuration the collet driver compresses the deformable collet, and the deformable collet compresses around the capture catheter and statically couples the capture catheter to the controller housing; and in the unlocked configuration the collet driver is relaxed from the deformable collet relative to the locked configuration and the deformable collet expands around the capture catheter and statically decouples the capture catheter relative to the controller housing.

2. The thrombectomy assembly of claim 1 comprising the capture catheter.

3. The thrombectomy assembly of claim 2, wherein the capture catheter includes a capture shaft and at least one deployable cage coupled with the capture shaft.

4. The thrombectomy assembly of claim 1, wherein in the unlocked configuration at least longitudinal movement of the controller housing moves at least the trumpet catheter relative to the capture catheter; and in the locked configuration at least longitudinal movement of the controller housing moves the trumpet catheter and the capture catheter together.

5. The thrombectomy assembly of claim 1, wherein rotation of the catheter lock in a first direction is configured to initiate the locked configuration; and rotation of the catheter lock in a second direction is configured to initiate the unlocked configuration.

6. The thrombectomy assembly of claim 1, wherein the catheter lock includes a lock body having a collet seat, and the deformable collet is received in the collet seat.

7. The thrombectomy assembly of claim 6, wherein the collet driver is movably coupled with the lock body.

8. The thrombectomy assembly of claim 7, wherein the collet driver movably coupled with the lock body includes the collet driver rotatably coupled with the lock body with a threaded interface.

9. The thrombectomy assembly of claim 6, wherein the lock body includes a trumpet seat, and the trumpet catheter is received in the trumpet seat.

10. The thrombectomy assembly of claim 1 comprising:
- a sheath catheter with a sheath lumen, wherein the trumpet catheter is received in the sheath lumen;
- wherein the manipulation controller includes a sheath actuator movably coupled with the controller housing, and the sheath actuator is configured to move the sheath catheter relative to the trumpet catheter and transition the deployable trumpet between a stored configuration with the deployable trump compressed and a deployed configuration with the deployable trump expanded.

11. A thrombectomy assembly comprising:
- a sheath catheter including a sheath lumen;
- a trumpet catheter including a trumpet lumen, the trumpet catheter having a deployable trumpet proximate to a trumpet catheter distal portion, the trumpet catheter is received in the sheath lumen;
- a manipulation controller configured to actuate the sheath catheter and the trumpet catheter, the manipulation controller includes:
  - a controller housing coupled with the trumpet catheter; and
  - a sheath actuator coupled with the sheath catheter, the sheath actuator is movable relative to the controller housing and configured to move the sheath catheter relative to the trumpet catheter;
  - wherein the sheath actuator includes:
    - an actuator shuttle movably coupled along an actuator track of the controller housing; and
    - at least one anchor, and the controller housing includes at least one anchor socket;
  - wherein the deployable trumpet includes deployed and stored configurations:
    - in the stored configuration the sheath actuator is in a first position relative to the controller housing, and the sheath catheter extends over the deployable trumpet; and
    - in the deployed configuration the sheath actuator is in a second position relative to the controller housing, the sheath catheter is retracted from the deployable trumpet, and the deployable trumpet is expanded relative to the stored configuration.

12. The thrombectomy assembly of claim 11, wherein the controller housing includes a trumpet seat, and the trumpet seat anchors a trumpet catheter proximal portion of the trumpet catheter with the controller housing.

13. The thrombectomy assembly of claim 12, wherein the sheath actuator includes a sheath seat, and the sheath seat anchors a sheath catheter proximal portion of the sheath catheter, and the sheath actuator and sheath catheter are movable together relative to the trumpet catheter.

14. The thrombectomy assembly of claim 11, wherein the actuator shuttle includes a trumpet catheter passage, the trumpet catheter is received in the trumpet catheter passage, and the actuator shuttle is slidably coupled with the trumpet catheter.

15. The thrombectomy assembly of claim 11, wherein the at least one anchor socket includes a retracted anchor socket, and in the deployed configuration the at least one anchor is received in the retracted anchor socket.

16. The thrombectomy assembly of claim 15, wherein the at least one anchor socket includes an extended anchor socket, and in the stored configuration the at least one anchor is received in the extended anchor socket.

17. The thrombectomy assembly of claim 11, wherein sheath actuator includes at least one anchor biasing element coupled with the at least one anchor, the at least one anchor biasing element is configured to bias the anchor toward the at least one anchor socket.

18. The thrombectomy assembly of claim 11, wherein the manipulation controller includes a catheter lock coupled with the controller housing, the catheter lock includes:
- a deformable collet having a collet passage configured to receive a capture catheter therein, the collet passage aligned with the trumpet lumen; and
- a collet driver coupled with the deformable collet.

19. The thrombectomy assembly of claim 18, wherein the catheter lock includes locked and unlocked configurations:
- in the locked configuration the collet driver longitudinally compresses the deformable collet, and the deformable collet compresses around the capture catheter and statically couples the capture catheter to the controller housing; and
- in the unlocked configuration the collet driver is relaxed from the deformable collet relative to the locked configuration and the deformable collet expands around the capture catheter and statically decouples the capture catheter relative to the controller housing.

20. The thrombectomy assembly of claim 18 comprising the capture catheter.

21. A thrombectomy assembly comprising:
- a sheath catheter including a sheath lumen;
- a trumpet catheter including a trumpet lumen configured to receive a capture catheter therein, the trumpet catheter having a deployable trumpet, and the trumpet catheter is received in the sheath lumen; and
- a manipulation controller coupled with the trumpet catheter and the sheath catheter, the manipulation controller includes:
- a controller housing coupled with the trumpet catheter;
- a sheath actuator coupled with the sheath catheter, the sheath actuator is movably coupled with the controller housing; and
- a catheter lock coupled with the controller housing, the catheter lock includes a deformable collet having a collet passage configured to receive the capture catheter therein, the collet passage aligned with the trumpet lumen;
- wherein the sheath actuator is configured to move the sheath catheter between a deployed configuration with the sheath actuator retracted from the deployable trumpet and a stored configuration with the sheath actuator covering the deployable trumpet; and
- wherein the deformable collet is configured to transition between a locked configuration with the deformable collet compressed around the capture catheter and the controller housing is statically coupled to the capture catheter and an unlocked configuration with the deformable collet expanded around the capture catheter and the controller housing is statically decoupled relative to the capture catheter.

22. The thrombectomy assembly of claim 21, wherein the sheath actuator includes a sheath seat, and the sheath seat anchors a sheath catheter proximal portion of the sheath catheter, and the sheath actuator and sheath catheter are movable together relative to the trumpet catheter.

23. The thrombectomy assembly of claim 21, wherein the sheath actuator includes a trumpet catheter passage, the trumpet catheter is received in the trumpet catheter passage, and the sheath actuator is slidably coupled with the trumpet catheter.

24. The thrombectomy assembly of claim 21, wherein the sheath actuator includes at least one anchor, and the controller housing includes at least one anchor socket.

25. The thrombectomy assembly of claim 24, wherein the at least one anchor socket includes:

a retracted anchor socket, and in the deployed configuration the at least one anchor is received in the retracted anchor socket; and an extended anchor socket, and in the stored configuration the at least one anchor is received in the extended anchor socket.

26. The thrombectomy assembly of claim 24, wherein sheath actuator includes at least one anchor biasing element coupled with the at least one anchor, the at least one anchor biasing element is configured to bias the anchor toward the at least one anchor socket.

27. The thrombectomy assembly of claim 21 wherein in the unlocked configuration at least longitudinal movement of the controller housing moves the trumpet catheter and the sheath catheter relative to the capture catheter; and in the locked configuration at least longitudinal movement of the controller housing moves the trumpet catheter, the sheath and catheter and the capture catheter together.

28. The thrombectomy assembly of claim 21, wherein rotation of the catheter lock in a first direction is configured to initiate the locked configuration; and rotation of the catheter lock in a second direction is configured to initiate the unlocked configuration.

29. The thrombectomy assembly of claim 21, wherein the catheter lock includes collet driver movably coupled with the deformable collet.

30. The thrombectomy assembly of claim 29, wherein in the locked configuration the collet driver longitudinally compresses the deformable collet, and the deformable collet radially compresses around the capture catheter according to the longitudinal compression; and in the unlocked configuration the collet driver is relaxed from the deformable collet relative to the locked configuration, and the deformable collet radially relaxes from the capture catheter according to the relaxing of the collet driver.

31. The thrombectomy assembly of claim 21 comprising the capture catheter.

32. The thrombectomy assembly of claim 31, wherein the capture catheter includes a capture shaft and at least one deployable cage coupled with the capture shaft.

* * * * *